United States Patent
Baskaran et al.

(10) Patent No.: US 10,822,723 B2
(45) Date of Patent: Nov. 3, 2020

(54) FUSION PROTEIN CRYSTAL COMPRISING A MOIETY

(71) Applicant: Agency for Science, Technology and Research, Singapore (SG)

(72) Inventors: Yohendran Baskaran, Singapore (SG); Robert Robinson, Singapore (SG); Edward Manser, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 31 days.

(21) Appl. No.: 15/771,863

(22) PCT Filed: Oct. 31, 2016

(86) PCT No.: PCT/SG2016/050533
§ 371 (c)(1),
(2) Date: Apr. 27, 2018

(87) PCT Pub. No.: WO2017/074268
PCT Pub. Date: May 4, 2017

(65) Prior Publication Data
US 2018/0266014 A1    Sep. 20, 2018

(30) Foreign Application Priority Data
Oct. 29, 2015   (SG) .............................. 10201508927S

(51) Int. Cl.
| | | |
|---|---|---|
| *C30B 29/58* | (2006.01) | |
| *C12N 9/12* | (2006.01) | |
| *C07K 14/47* | (2006.01) | |
| *C30B 29/66* | (2006.01) | |
| *G01N 23/205* | (2018.01) | |
| *C12N 15/62* | (2006.01) | |
| *G01N 23/2055* | (2018.01) | |

(52) U.S. Cl.
CPC .......... *C30B 29/58* (2013.01); *C07K 14/4703* (2013.01); *C12N 9/12* (2013.01); *C12Y 207/11001* (2013.01); *C30B 29/66* (2013.01); *G01N 23/2055* (2013.01); *C07K 2319/00* (2013.01); *C07K 2319/43* (2013.01); *C12N 15/62* (2013.01); *C12Y 207/11022* (2013.01); *G01N 2223/612* (2013.01)

(58) Field of Classification Search
None
See application file for complete search history.

(56) References Cited

U.S. PATENT DOCUMENTS
2011/0171714 A1   7/2011   Cheetham et al.

FOREIGN PATENT DOCUMENTS
| | | |
|---|---|---|
| WO | 01/85962 A1 | 11/2001 |
| WO | 2012/158555 A2 | 11/2012 |

OTHER PUBLICATIONS

Schönherr et al., "Real-time investigation of dynamic protein crystallization in living cells", Structural Dynamics 2, 041712 (2015), pp. 1-17.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Moon et al., "A synergistic approach to protein crystallization: Combination of a fixed-arm carrier with surface entropy reduction", Protein Science, 2010, 19:901-913.*
McPherson & Gavira, "Introduction to protein crystallization", Acta Crystallographica Section F Structural Biology Communications, 2014, F70, pp. 2-20.*
Ha et al., "Type II p21-activated kinases (PAKs) are regulated by an autoinhibitory pseudosubstrate", PNAS, 2012, vol. 109, No. 40 , pp. 16107-16112. doi/10.1073/pnas.1214447109.*
Suzuki et al., "Crystallization of small proteins assisted by green fluorescent protein", Acta Crystallographica D, 2010, D66, pp. 1059-1066. doi.org/10.1107/S0907444910032944.*
Baskaran et al., "An in cellulo-derived structure of PAK4 in complex with its inhibitor Inka1," *Nature Communications* 6:8681, 2015, 11 pages.
Ijiri et al., "Structure-based targeting of bioactive proteins into cypovirus polyhedra and application to immobilized cytokines for mammalian cell culture," *Biomaterials* 30:4297-4308, 2009.
Luo et al., "Inca: a novel p21-activated kinase-associated protein required for cranial neural crest development," *Development* 134:1279-1289, 2007.
Wang et al., "Assembly of Multivalent Protein Ligands and Quantum Dots: A Multifaceted Investigation," *Langmuir* 30:2161-2169, 2014.

* cited by examiner

*Primary Examiner* — Suzanne M Noakes
(74) *Attorney, Agent, or Firm* — Seed IP Law Group LLP

(57) ABSTRACT

A protein crystal comprising a first protein crystal having available space in the lattice, wherein a second protein crystal and a moiety can be accommodated in the available space in the lattice. The first and second proteins are co-expressed from one or more nucleic acid constructs. In a preferred embodiment, the first protein is the p21-activated kinase PAK4, the second protein is the PAK4 kinase inhibitor Inka1, and the moiety comprises a reporter molecule such as fluorescent proteins or tags and is fused to the iBox or iBox-C or Inka1. Preferably the crystal is formed in cellulo. Also provided is a fusion protein comprising the first protein and the second protein, wherein upon crystallisation the second protein fits within the available space in the lattice of the first protein, along with the moiety. Methods for producing the protein crystal are also disclosed.

17 Claims, 13 Drawing Sheets

Figure 1:
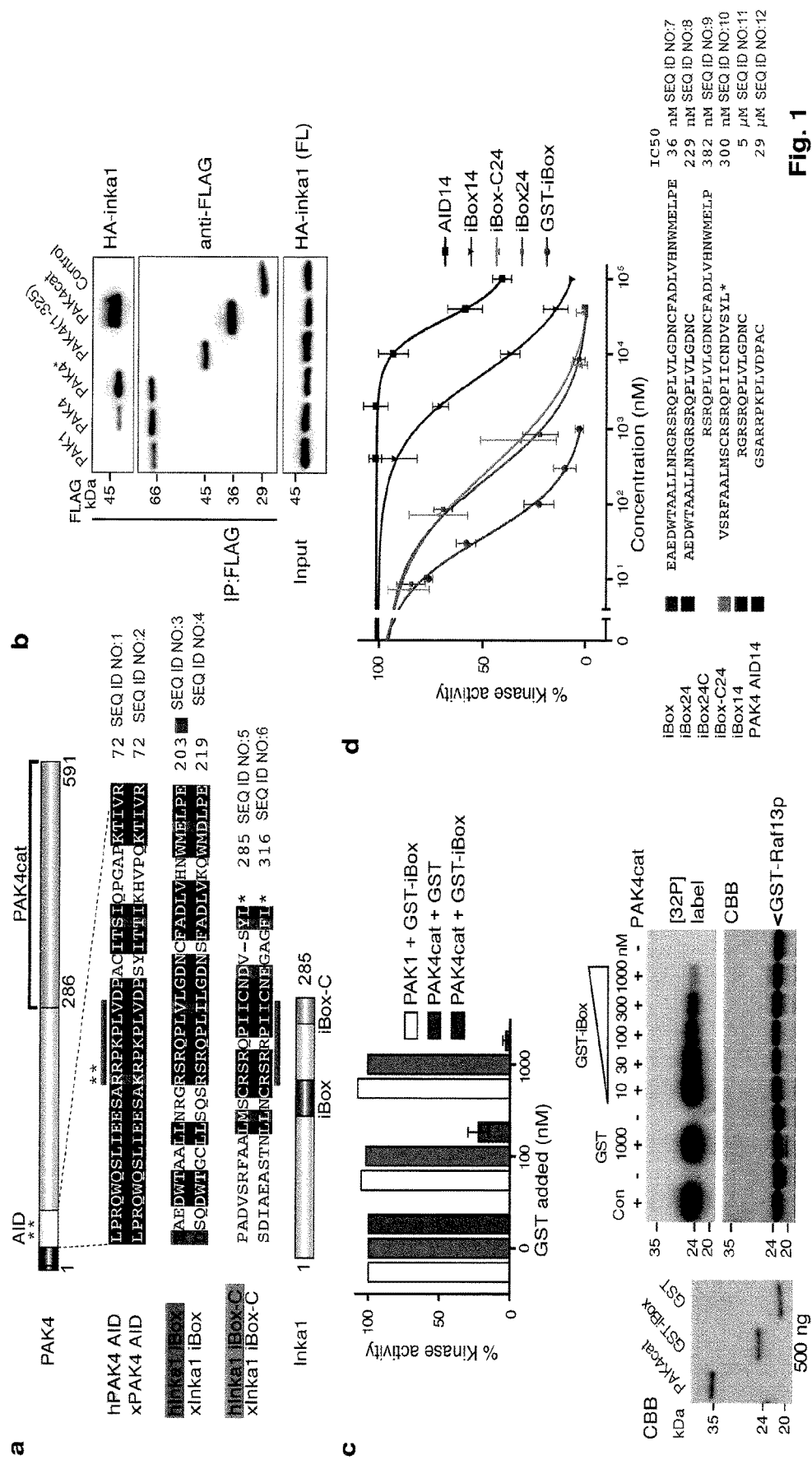

Specification includes a Sequence Listing.

PKIalpha : PKA (ADP)

1RDQ

Inka1 : PAK4 (ATP)

p16INK4 : CDK6

1BI7 p27KIP : CDK2 : cyclinA

1JSU

US 10,822,723 B2

FUSION PROTEIN CRYSTAL COMPRISING A MOIETY

STATEMENT REGARDING SEQUENCE LISTING

The Sequence Listing associated with this application is provided in text format in lieu of a paper copy, and is hereby incorporated by reference into the specification. The name of the text file containing the Sequence Listing is 100216_401_USPC_SEQUENCE_LISTING.txt. The text file is 7.6 KB, was created on May 18, 2020, and is being submitted electronically via EFS-Web.

The present invention relates to in cellulo derived structures. In particular, the present invention relates to an in cellulo derived protein structure of PAK4 in complex with its inhibitor Inka1. The present invention also discloses structure protein crystallography methods and constructs useful therein.

Proteins are involved in a multitude of biological processes. High resolution structural data has allowed useful insight into the function of a number of proteins. Despite these successes the number of resolved protein structures remains extremely small compared with soluble proteins. Crystallization is necessary to obtain the three-dimensional structure of proteins; it often represents the bottleneck in structure determination. As such, there is a need to develop a platform to rapidly generate crystals with proteins that might otherwise be difficult to express (in bacteria or insect cells) and/or crystallise in vitro.

Here, we describe the structure of human PAK4 in complex with Inka1, an endogenous inhibitor of the kinase. Using single mammalian cells containing crystals 50 µm in length we have determined the in cellulo crystal structure at 2.95 Å resolution, which reveals the details of how the PAK4 catalytic domain (cat) binds cellular ATP and the Inka1 inhibitor. The crystal lattice consists only of PAK4-PAK4 contacts, which form an hexagonal array with channels of 80 Å in diameter that run the length of the crystal. We have demonstrated that the crystal accommodates a variety of other proteins when fused to full-length or fragments of Inka1 that contain the inhibitory sequence. These crystals can form when the proteins are expressed as a single polypeptide chain, or when various Inka1 protein fragments are expressed separately from PAK4cat. Inka1-GFP was used to monitor the process crystal formation in living cells. Similar derivatives of Inka1 will allow us to study the effects of PAK4 inhibition in cells and model organisms, to allow better validation of therapeutic agents targeting PAK4.

Mammalian PAK isoforms are categorized into two groups on the basis of their structural and biochemical features: the conventional or group I PAKs in human comprise PAKs1-3, while the group II PAKs (PAK4-6) are encoded by three genes in mammals. PAK4-like kinases are ubiquitously expressed in metazoans, but not found in protozoa or fungi. This is consistent with PAK4 functioning primarily at cell-cell contacts in mammalian cells, with Cdc42 also being required for adherent junction formation. The phenotype of PAK4-null mice, which is embryonic lethal, involves defects in the fetal heart as well as in neuronal development and axonal outgrowth[8]. The loss of PAK4 prevents proper polarization and thus formation of the endothelial lumen[9], consistent with defects seen in PAK4−/− mice.

PAK4 is a kinase with strong links to cellular transformation and cancer metastasis. The structural basis for PAK4's preference for serine containing substrate sites has recently been elucidated. We have shown that Cdc42 directly regulates PAK4 activity in mammalian cells through an auto-inhibitory domain (AID) that binds in a manner similar to pseudo-substrates [1, 2]. This is consistent with the notion that PAK4 lacking residues 10-30 in the Cdc42/Rac interactive binding (CRIB) domain is active. Although PAK1 activation in vivo occurs through activation loop Thr-423 phosphorylation, it is notable that PAK4 is constitutively phosphorylated on Ser-474[1], and kept in check through the intra-molecular association of the AID. The binding of Cdc42 can serve to activate PAK4 in cells, but it is unclear if there is any auto-phosphorylation event associated with this activation [1]. Since PAK4 does not appear to utilize adaptors we investigated the possibility that Inka1, first identified as a PAK4 binding protein in frogs, might fulfill this role.

In vivo protein crystallization is rare with mammalian examples including insulin and Charcot-Leyden crystals. The observation that hemoglobin could crystallize upon dilution of unpurified red cell lysate facilitated the advent of protein X-ray crystallography. Only recently have microcrystals generated inside bacterial or insect cells become amenable to X-ray analysis [3-5]. A coral fluorescent protein that forms diffraction-quality micron-sized crystals within mammalian cells [6] indicates the mammalian cell environment could be suitable host for a number of proteins, which are not normally crystalline.

Experiments described here suggest that Inka proteins are in fact endogenous inhibitors of PAK4, with the two human Inka isoforms sharing a high degree of sequence identity in the region previously termed the Inca box. Inka1 contains an additional PAK4 inhibitory sequence at its C-terminus, and either of these sequences can promote crystallization of the catalytic domain of human PAK4 in mammalian cells. An in-cellulo protein structure, from X-ray experiments on single crystals formed within a mammalian cell reveals a hexagonal array the PAK4cat subunits that was suggestive of an ability accommodate other proteins in the lattice. This was demonstrated by fusing Inka1 to GFP. Because of these features the PAK4 array has potential as a protein analogue of 'crystalline molecular flasks' in which guest molecules can reside to facilitate their X-ray analysis [7].

The listing or discussion of an apparently prior-published document in this specification should not necessarily be taken as an acknowledgement that the document is part of the state of the art or is common general knowledge.

Any document referred to herein is hereby incorporated by reference in its entirety.

In a first aspect of the present invention, there is provided a protein crystal comprising: (a) a first protein crystal having available space in the lattice; and (b) a second protein crystal to be accommodated in the available space in the lattice, the first and second proteins are co-expressed from one or more nucleic acid construct, wherein the crystal further accommodates a moiety in the available space in the lattice.

By "protein crystal", it is meant to refer to a form of the solid state of matter having a three-dimensional crystal lattice, which is distinct from the amorphous or semi-crystalline state. Crystals display characteristic features, including a lattice structure, characteristic shapes and optical properties, such as, e.g., birefringence. Determination as to whether a protein is in a crystalline state may be carried out by any method known in the art, e.g., X-ray diffraction or powder X-ray diffraction or transmission electron microscopy (TEM).

X-ray crystallography is a fundamental tool used for identifying the atomic and molecular structure of many materials which can form crystals, such as metals or minerals, as well as various inorganic, organic and biological molecules. For example, the three-dimensional structure of a protein determines its function; consequently, structural insights into proteins at atomic resolution are important to understand the machinery of life or to develop new specifically designed drugs for medical applications. This technique requires sufficiently large crystals to obtain structural insights at atomic resolution, routinely obtained in vitro by time-consuming screening. As such, with the present invention, successful structural information can be obtained from tiny protein microcrystals grown within living cells, offering exciting new possibilities for proteins that do not form crystals in vitro.

It will be appreciated that the crystal lattice is formed by the protein which makes and maintains most of the crystal contacts within the lattice, and that the crystal lattice itself may be altered by the presence of a second protein. Assuming there was an alteration, such an altered crystal lattice is included in our definition of "crystal lattice".

"Co-crystallization" may also be used to define and describe the crystallization of the two proteins. It is defined as two different materials crystallizing into the same crystalline lattice. For example, a monovalent cation, divalent cation or polycation may crystallize into the same crystalline lattice as a protein having a negatively-charged side chains. By "co-crystals" is meant a complex of the compound, molecular scaffold, or ligand bound non-covalently to the target molecule and present in a crystal form appropriate for analysis by X-ray or protein crystallography. The entire protein crystal comprising the two proteins may be co-expressed from a single (or more) nucleic acid construct.

The said "space" may be utilized to accommodate the second protein. For example, it may allow the second protein to pack in an ordered manner (or in any manner depending on its interaction with the first protein) into the crystal lattice of the first protein, which may be used as a "scaffold" molecule.

By "co-expression", it is meant to refer to expression of both first and second proteins in cellulo or in vitro. The first and second proteins may form a single protein chain, or may be from separate entities or polypeptide chains. Likewise, any nucleic acid(s) that encode the protein crystal may be from one or more nucleic acid construct.

In embodiment, the first protein is a kinase and the second protein is an inhibitor of the kinase.

The second protein may be an inhibitor of kinase activity. More preferably, the inhibitor of kinase activity is Inka1, or a fragment thereof.

Preferably, the first protein is a p21-activated kinase. More preferably, the kinase is PAK4. Still more preferably, the PAK4 is the catalytic domain of PAK4.

In an embodiment the moiety is fused with either the first or second protein. Alternatively, the moiety may not be crystallised.

Preferably, the moiety is fused to iBox or iBox-C of Inka1.

The moiety is a protein of interest likely having a molecular mass of less than 30 kDa. The moiety may also be a reporter molecule. For example, the reporter molecule may be any one selected from the group comprising: fluorescent proteins, tags recognized by monoclonal antibodies, genetically encoded biosensors and the like. The molecules may be selected to respond to changes in intracellular or in-vitro environments, or externally applied chemicals or drugs.

The present invention may be used for performing high throughput screening of crystallization of target materials, proteins, or any other moiety. Potential fields of use include microbiology, chemical synthesis, high throughput screening, drug discovery, medical diagnostics, pathogen identification, and enzymatic reactions.

In addition, the present invention may be used to do exhaustive screening of protein crystallization conditions. This screening may be done in a random or systematic way. Alternatively, where high throughput screening in accordance with embodiments of the present invention does not produce crystals of sufficient size for direct X-ray crystallography, the crystals can be utilized as seed crystals for further crystallisation experiments. Promising screening results can also be utilized as a basis for further screening focusing on a narrower spectrum of crystallisation conditions, in a manner analogous to the use of standardised sparse matrix techniques.

Preferably, the protein crystal forms a hexagonal array with channels of 80 Å in diameter.

Preferably, the ratio of the first protein to the second protein 1:1.

In an embodiment, each first and second protein may contain domains that allows it to dimerize or multimerize with each other and/or to other proteins. The domain that functions to dimerize or multimerize the proteins can either be a separate domain, or alternatively can be contained within one of the other domains of the protein. Preferably, such dimeric proteins result in a protein crystal having available space in its lattice structure to accommodate the moiety. The moiety or combination of moieties may be of any suitable size. In an embodiment, the moiety may have a molecular size of less than 30 kDa. Alternatively, the moiety may have a molecular size of more than 30 kDa, for example the molecular size of the moiety may be 40 kDa, 50 kDa, 60 kDa, 65 kDa or more.

Dimerization or multimerization can occur between or among two or more of the proteins through dimerization or multimerization domains. Alternatively, dimerization or multimerization of the proteins can occur by chemical crosslinking. The dimers or multimers that are formed can be homodimeric/homomultimeric or heterodimeric/heteromultimeric.

A "dimerization domain" is formed by the association of at least two amino acid residues or of at least two peptides or polypeptides (which may have the same, or different, amino acid sequences). The peptides or polypeptides may interact with each other through covalent and/or non-covalent association(s). Preferred dimerization domains contain at least one cysteine that is capable of forming an intermolecular disulfide bond with a cysteine on the partner protein. The dimerization domain can contain one or more cysteine residues such that disulfide bond(s) can form between the partner proteins. In one embodiment, dimerization domains contain one, two or three to about ten cysteine residues.

Additional exemplary dimerization domain can be any known in the art and include, but not limited to, coiled coils, acid patches, zinc fingers, calcium hands, a $C_H1$-$C_L$ pair, an "interface" with an engineered "knob" and/or "protruberance" as described in U.S. Pat. No. 5,821,333, leucine zippers (e.g., from jun and/or fos) (U.S. Pat. No. 5,932,448), SH2 (src homology 2), SH3 (src Homology 3) (Vidal, et al., Biochemistry, 43, 7336-44 ((2004)), phosphotyrosine binding (PTB) (Zhou, et al., Nature, 378:584-592 (1995)), WW (Sudol, Prog. Biochys. Mol. Bio., 65:113-132 (1996)), PDZ (Kim, et al., Nature, 378: 85-88 (1995); Komau, et al., Science, 269:1737-1740 (1995)) 14-3-3, WD40 (Hu, et al., J Biol Chem., 273, 33489-33494 (1998)) EH, Lim, an isoleucine zipper, a receptor dimer pair (e.g., interleukin-8 receptor (IL-8R); and integrin heterodimers such as LFA-1 and GPIIIb/IIIa), or the dimerization region(s) thereof, dimeric ligand polypeptides (e.g. nerve growth factor (NGF), neurotrophin-3 (NT-3), interleukin-8 (IL-8), vascular endothelial growth factor (VEGF), VEGF-C, VEGF-D, PDGF members, and brain-derived neurotrophic factor (BDNF) (Arakawa, et al., J Biol. Chem., 269(45): 27833-27839 (1994) and Radziejewski, et al., Biochem., 32(48): 1350 (1993)) and can also be variants of these domains in which the affinity is altered. The polypeptide pairs can be identified by methods known in the art, including yeast two hybrid screens. Yeast two hybrid screens are described in U.S. Pat. Nos. 5,283,173 and 6,562,576, both of which are herein incorporated by reference in their entireties. Affinities between a pair of interacting domains can be determined using methods known in the art, including as described in Katahira, et al., J. Biol. Chem., 277, 9242-9246 (2002)). Alternatively, a library of peptide sequences can be screened for heterodimerization, for example, using the methods described in WO 01/00814. Useful methods for protein-protein interactions are also described in U.S. Pat. No. 6,790,624.

A "multimerization domain" is a domain that causes three or more peptides or polypeptides to interact with each other through covalent and/or non-covalent association(s). Suitable multimerization domains include, but are not limited to, coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, Ile, Leu, Met, Tyr, Phe and Trp. Mainly hydrophobic means that at least 50% of the residues must be selected from the mentioned hydrophobic amino acids.

The coiled coil domain may be derived from laminin. In the extracellular space, the heterotrimeric coiled coil protein laminin plays an important role in the formation of basement membranes. Apparently, the multifunctional oligomeric structure is required for laminin function. Coiled coil domains may also be derived from the thrombospondins in which three (TSP-1 and TSP-2) or five (TSP-3, TSP-4 and TSP-5) chains are connected, or from COMP (COMPcc) (Guo, et at., EMBO J., 1998, 17: 5265-5272) which folds into a parallel five-stranded coiled coil (Malashkevich, et al., Science, 274: 761-765 (1996)). Additional coiled-coil domains derived from other proteins, and other domains that mediate polypeptide multimerization are known in the art and are suitable for use in the present proteins.

Advantageously, and importantly, the expression of the protein and the subsequent crystallization occur in cellulo. In an embodiment, the protein and crystallization of the protein occurs in a mammalian cell. The mammalian cell may be any cell, including one that may be a part of a transgenic animal. Alternatively, the recombinant kinase and inhibitor proteins are made and purified from other species, such as E. coli, and mixed to promote crystallization either in-vivo or in-vitro.

Preferably, the crystal may be of any size that is suitable for X-ray crystallography. In an embodiment, the crystal is >50 µm in length and the crystal structure determined at <3 Å resolution.

Advantageously, the present invention makes use of a PAK4 scaffold to generate high quality protein crystals in mammalian cells by co-expression with inhibitory protein Inka1 (or a fragment thereof) fused to a protein of interest (third party protein or any moiety of choice).

In a second aspect of the present invention, there is provided one or more isolated polypeptide molecule having a sequence or sequences that encode a protein or proteins which, upon crystallisation, form a protein crystal according to the first aspect of the present invention. In other words, the protein crystal may be expressed in a single or separate construct expression system.

The protein molecules may be full-length or fragments thereof, so long as these sequences promote crystallization. For example, the kinase PAK4 may be any suitable sequence and its inhibitor Inka1 may contain any inhibitory sequence. It would be understood by those in the art that a variant or mutation to the protein sequences could be used to promote crystallization wherein at one or more positions there have been insertions, deletions, or substitutions, either conservative or non-conservative, provided that such changes result in a sequence whose basic properties, for example promoting crystallization have not significantly been changed. "Significantly" in this context means that one skilled in the art would say that the properties of the variant may still be different but would not be unobvious over the ones of the original protein sequences.

In a third aspect of the present invention, there is provided a fusion protein comprising: (a) a first protein, upon crystallisation, yields a crystal having available space in the lattice; and (b) a second protein crystal to be accommodated, upon crystallisation, in the available space in the lattice, the first and second proteins are co-expressed from one or more nucleic acid construct, wherein the lattice further accommodates a moiety in the available space. The fusion protein may be in a single or separate construct expression system.

In an embodiment, the fusion protein additionally contain a domain that allows it to dimerize or multimerize with each other and/or to other proteins.

In a fourth aspect of the present invention, there is provided one or more isolated nucleic acid molecule having a sequence or sequences that encode a protein or proteins which, upon crystallisation, form a protein crystal according to the first aspect of the present invention.

In a fifth aspect of the present invention, there is provided an expression vector or vector combinations or a cultured host cell harbouring one or more isolated nucleic acid molecule according to the fourth aspect of the present invention.

The native and mutated kinase and/or kinase inhibitor polypeptides described herein may be chemically synthesized in whole or part using techniques that are well-known in the art.

Methods which are well known to those skilled in the art can be used to construct expression vectors containing the polypeptide coding sequence and appropriate transcriptional/translational control signals. These methods include in vitro recombinant DNA techniques, synthetic techniques and in vivo recombination/genetic recombination. See, for example, the techniques described in Maniatis, T (1989). *Molecular cloning: A laboratory Manual*. Cold Spring Harbor Laboratory, New York. Cold Spring Harbor Laboratory Press; and Ausubel, F. M. et al. (1994) *Current Protocols in Molecular Biology*. John Wiley & Sons, Secaucus, N.J.

A variety of host-expression vector systems may be utilized to express the kinase-inhibitor coding sequence. These include but are not limited to microorganisms such as bacteria transformed with recombinant bacteriophage DNA, plasmid DNA or cosmid DNA expression vectors containing the coding sequence; yeast transformed with recombinant yeast expression vectors containing the domain coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The expression elements of these systems vary in their strength and specificities.

Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the $^{35}$S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the kinase domain DNA, SV40-, BPV- and EBV-based vectors may be used with an appropriate selectable marker.

Exemplary methods describing methods of DNA manipulation, vectors, various types of cells used, methods of incorporating the vectors into the cells, expression techniques, protein purification and isolation methods, and protein concentration methods are disclosed in detail in PCT publication WO 96/18738. This publication is incorporated herein by reference in its entirety, including any drawings. Those skilled in the art will appreciate that such descriptions are applicable to the present invention and can be easily adapted to it.

In a sixth aspect of the present invention, there is provided a method for producing a protein crystal structure or a fusion a protein comprising a first protein, upon crystallisation, yields a crystal having available space in the lattice; and a second protein is accommodated, upon crystallisation, in the available space in the lattice, the method comprising culturing a host cell under conditions that allow for the expression and/or production of the protein crystal or fusion protein, the first and second protein are co-expressed from one or more nucleic acid construct, wherein the crystal further accommodates a moiety in the available space in the lattice.

In an embodiment, the host cell may be a mammalian cell. Alternatively the optimal conditions can be selected to allow for crystallization in-vitro from purified proteins.

Preferably, the first protein is a kinase and the second protein is an inhibitor of the kinase. The kinase may be PAK4 and the kinase inhibitor may be Inka1, or a fragment thereof.

Preferably, the method further comprises fusing a moiety with the second protein, wherein the moiety is accommodated, upon crystallisation, in the available space in the lattice. Alternatively, the moiety may not be crystallised but may be a part of the crystal lattice structure. Still alternatively, the moiety may be fused with the first protein. The moiety being a protein of interest may have a molecular mass less than 30 kDa and may further comprise a reporter molecule fused to it.

Preferably, the method further comprises isolating and purifying the protein crystal.

Preferably, the method further comprising obtaining structural data on the crystal. Advantageously, the crystals are generated in mammalian cells so that they are of sufficient quality for X-ray structural analysis.

Computer models, such as homology models (i.e., based on a known, experimentally derived structure) can be constructed using data from the co-crystal structures. When the target molecule is a protein or enzyme, preferred co-crystal structures for making homology models contain high sequence identity in the binding site of the protein sequence being modeled, and the proteins will preferentially also be within the same class and/or fold family. Knowledge of conserved residues in active sites of a protein class can be used to select homology models that accurately represent the binding site. Homology models can also be used to map structural information from a surrogate protein where an apo or co-crystal structure exists to the target protein.

Virtual screening methods, such as docking, can also be used to predict the binding configuration and affinity of scaffolds, compounds, and/or combinatorial library members to homology models. Using this data, and carrying out "virtual experiments" using computer software can save substantial resources and allow the person of ordinary skill to make decisions about which compounds can be suitable scaffolds or ligands, without having to actually synthesize the ligand and perform co-crystallization. Decisions thus can be made about which compounds merit actual synthesis and co-crystallization. An understanding of such chemical interactions aids in the discovery and design of drugs that interact more advantageously with target proteins and/or are more selective for one protein family member over others. Thus, applying these principles, compounds with superior properties can be discovered.

In order that the present invention may be fully understood and readily put into practical effect, there shall now be described by way of non-limitative examples only preferred embodiments of the present invention, the description being with reference to the accompanying illustrative figures.

In the Figures:

FIG. 1. Inka1 is a potent kinase inhibitor (a) PAK4 architecture and alignment of the AID and the Inka1 iBox and iBox-C from frogs and human. Red asterisks indicate activation mutations in PAK4* (RR48/49AE). Red bars indicate pseudo-substrate sequences. (b) Co-immunoprecipitation of full-length HA-Inka1 by FLAG-tagged PAK4 constructs. (c) Kinase assays utilizing 6His-PAK1 (activated) or PAK4cat, with GST-iBox as indicated. Activity was assessed by the phosphorylation of GST-Raf13 quantified by densitometry (lower right). The quality of the purified proteins is indicated (lower left). (d) The inhibition profile of GST-iBox and selected peptides of the iBox and iBox-C (n=3, error bars indicate s.e.m). The $IC_{50}$ values were determined from the intercepts of the graphs.

Figure 2:
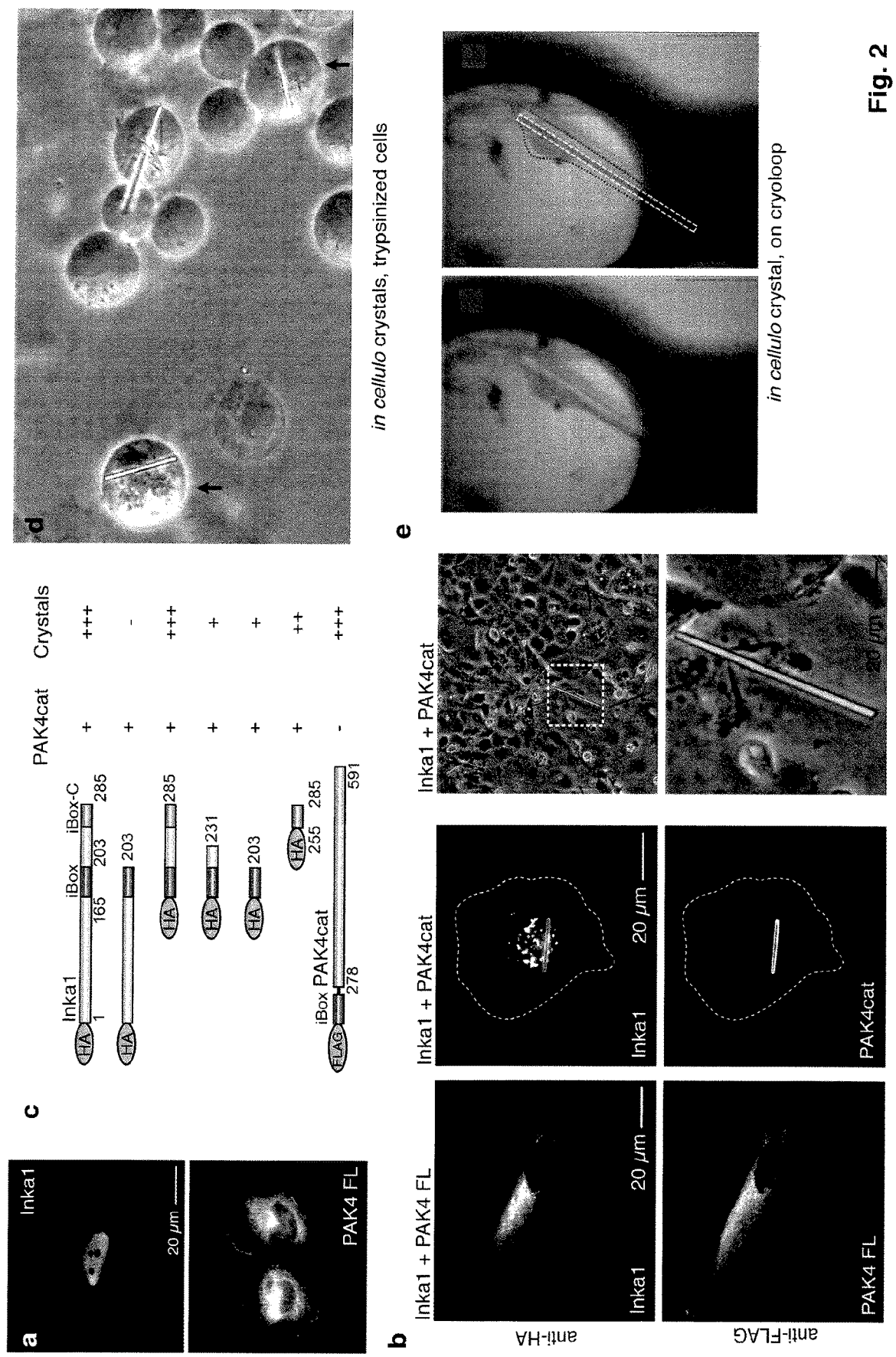

FIG. 2. Intracellular PAK4cat:Inka1 crystals (a) Inka1 and PAK4 show nuclear and cytoplasmic localization, respectively. (b) Co-expression leads to cytoplasmic enrichment of Inka1 (left panels). Inka1 and PAK4cat co-expression results in intracellular crystals (right panels), which immuno-stain for both proteins (middle panels). (c) Inka1 regions capable of generating co-crystals. A single chain fusion of iBox-PAK4cat efficiently generated intracellular crystals. (d) in cellulo crystals of trypsinized cells. (e)

A single cell mounted on a cryo-loop on a synchrotron beamline. The crystal (yellow), the cell membrane (red) and the nucleus (green) are highlighted.

Figure 3:
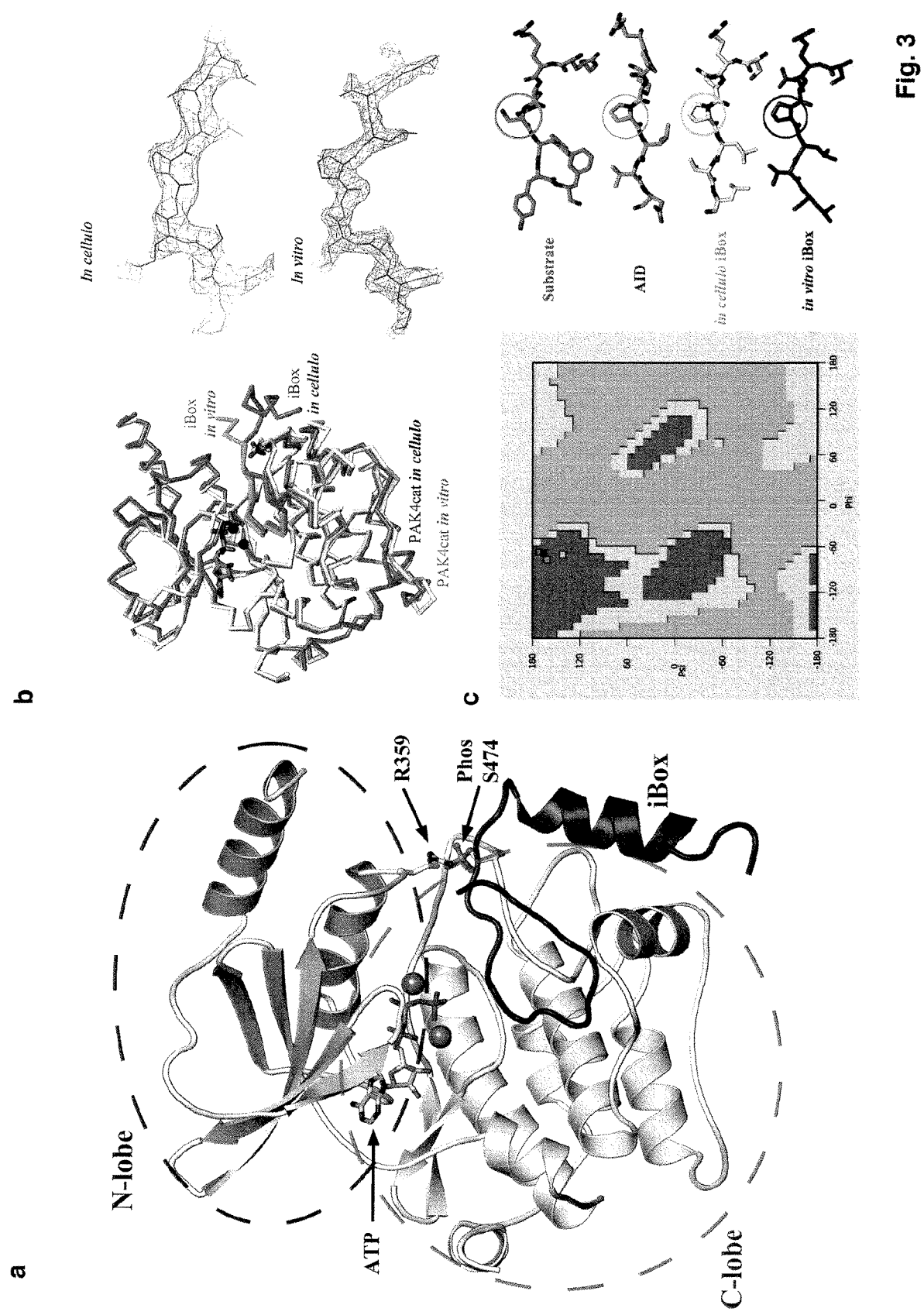

FIG. 3. The in cellulo X-ray structure of the catalytic domain of PAK4 in complex with Inka1

(a) The X-ray structure of the iBox-PAK4cat complex derived from diffraction the in vivo crystals. The typical kinase fold is observed with the iBox (red) binding the PAK4cat close to the phospho-Ser474 (orange), ATP, and magnesium ions (mustard). (b) Overlay of in vitro and in vivo PAK4cat: Inka1 complex structure. Comparison between the alpha carbon traces of Pak4cat: Inka crystallized in vivo (grey and red) and Pak4cat co-crystallized with a synthetic peptide iBox24 (see FIG. 1D). The PAK4cat with iBox24 yielded a structure at 2 Å, which was overlaid (backbone of the chains in yellow and cyan). The ATP and two $Mg^{2+}$, found in the in vivo structure, are represented in stick and sphere format. On the right is the comparison of the electron density maps of the Inka1 core sequence in the two structures. Stereo images of portions of the 2Fo-Fc electron density maps contoured at 1.5 sigma and centered at P(0) in Inka is provided in FIG. 13. (c) Conservation of the bond angles comparing the substrate serine with proline mimetic in Inka1. The local main-chain and side-chain orientation of the substrate serine (S0) and corresponding prolines in the substrate mimetics are as indicated. Values corresponding to these four residues are mapped onto the standard Ramachandran plot indicate their similar orientation.

Figure 4:
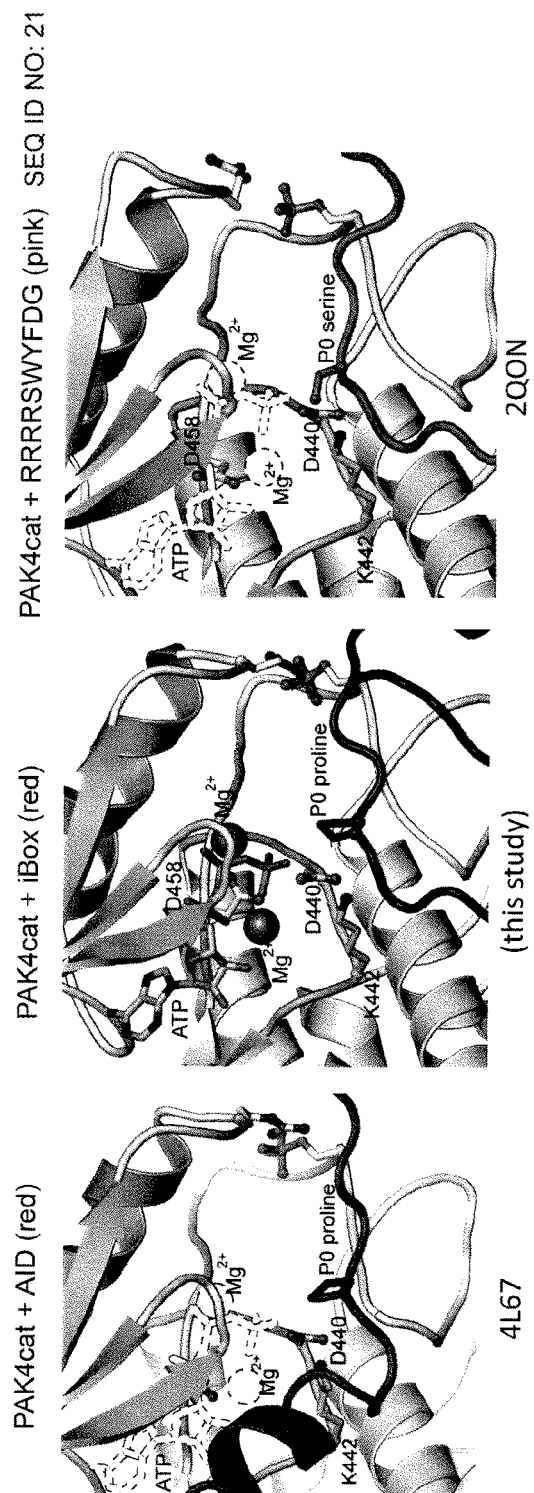
Figure 4:
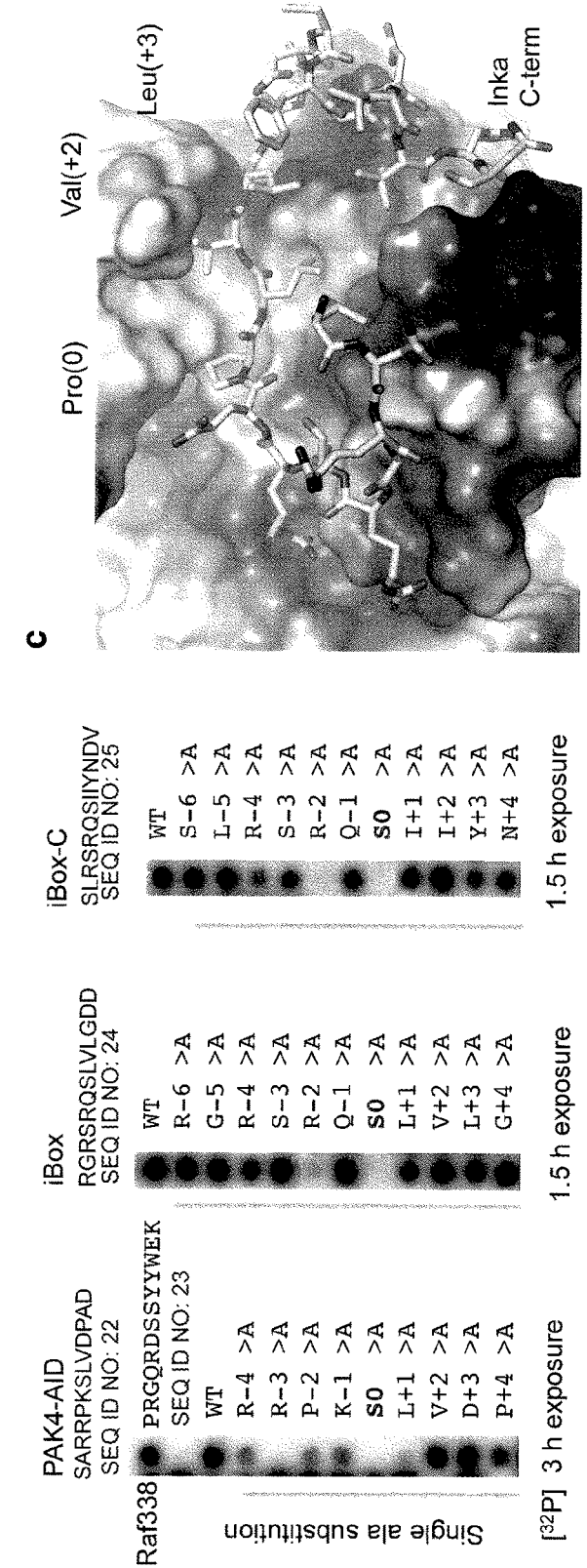

FIG. 4. Inka1 inhibition of PAK4 activity through substrate mimicry (a) Left-to-right: PAK4:AID (red); the in cellulo structure of PAK4:iBox (dark red); PAK4:substrate (purple). The inhibitor prolines (P0) are similarly positioned to the serine (S0) of the substrate. (b) To assess the inhibitors as 'supersubstrates' we tested 13aa synthetic peptides with Pro (0)Ser substitutions in an array. The contribution of each side chain to substrate binding was assessed via alanine substitutions. The Ser (0)Ala completely abolished phosphorylation in each case, confirming other Serines were not phosphorylated. (c) iBox-PAK4 in cellulo structure highlighting the cluster of hydrophobic contacts between the Inka1 side-chains and the surface of the PAK4 (yellow). The hydrogen bonds are marked in orange.

Figure 5:
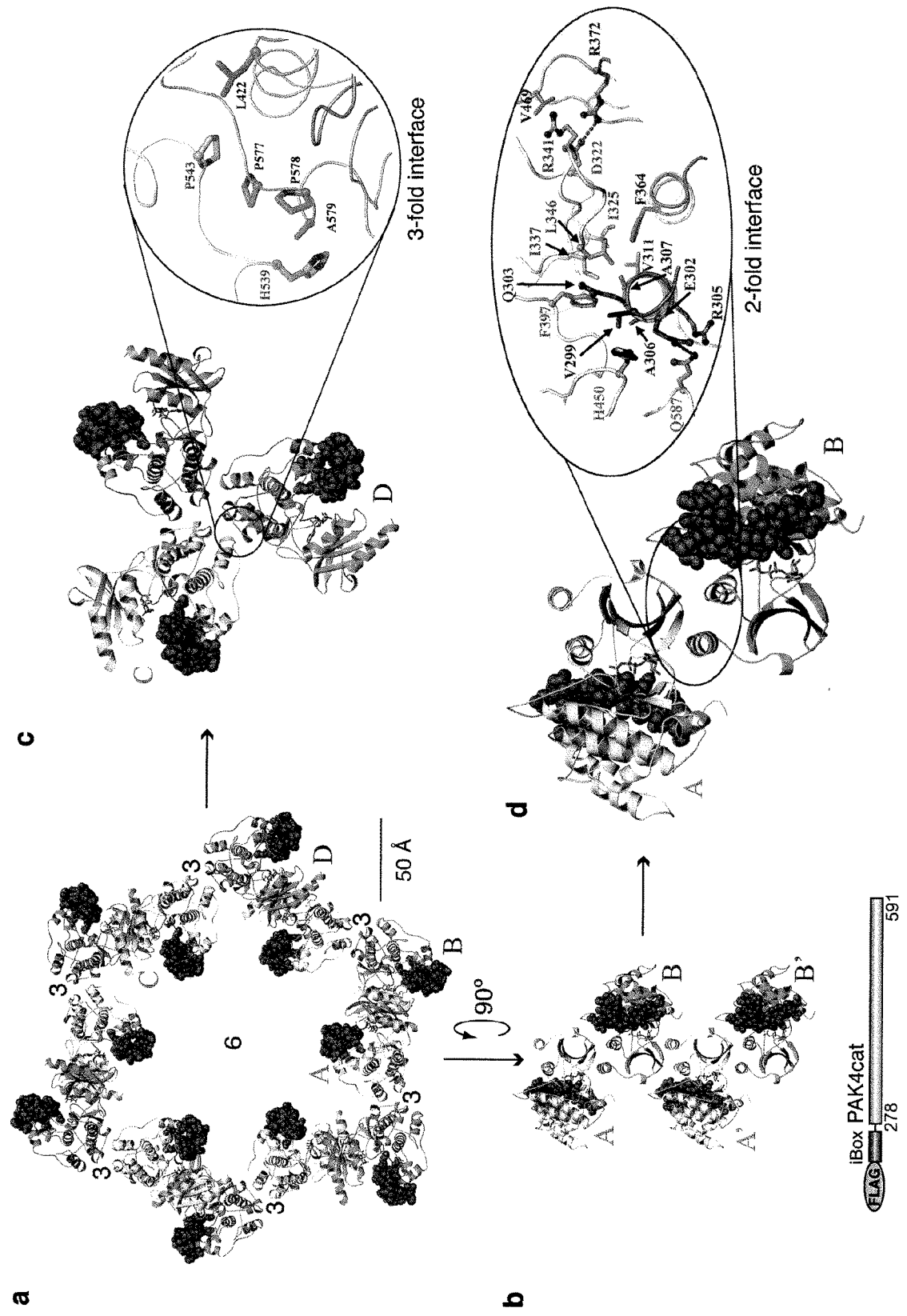

FIG. 5. Crystal packing of the PAK4cat: inKa crystals and the nature of the protein-protein interface (a) The in cellulo construct and crystal packing of PAK4cat which form the channel in the presence of Inka1 (red). The schematic of the construct is similarly coloured. (b) the N-lobes which form the strands that run along the length of the channel. (c) The 3-fold axis involves hydrophobic interactions of the C-lobe, primarily involving proline residues as indicated. (d) The 2-fold interface involves primarily hydrophobic side-chain interactions between the B subunit (blue) N-lobe α-helices including the F364 in the α-helix-C, which interacts with the beta-strand sequences. The α-helix-C, a conserved feature of protein kinases coordinates PAK4 kinase activity. PAK4cat (alternately yellow and cyan) and iBox (red). Numbers indicate fold axes. This schematic was generated using PyMOL Molecular Graphics System.

Figure 6:
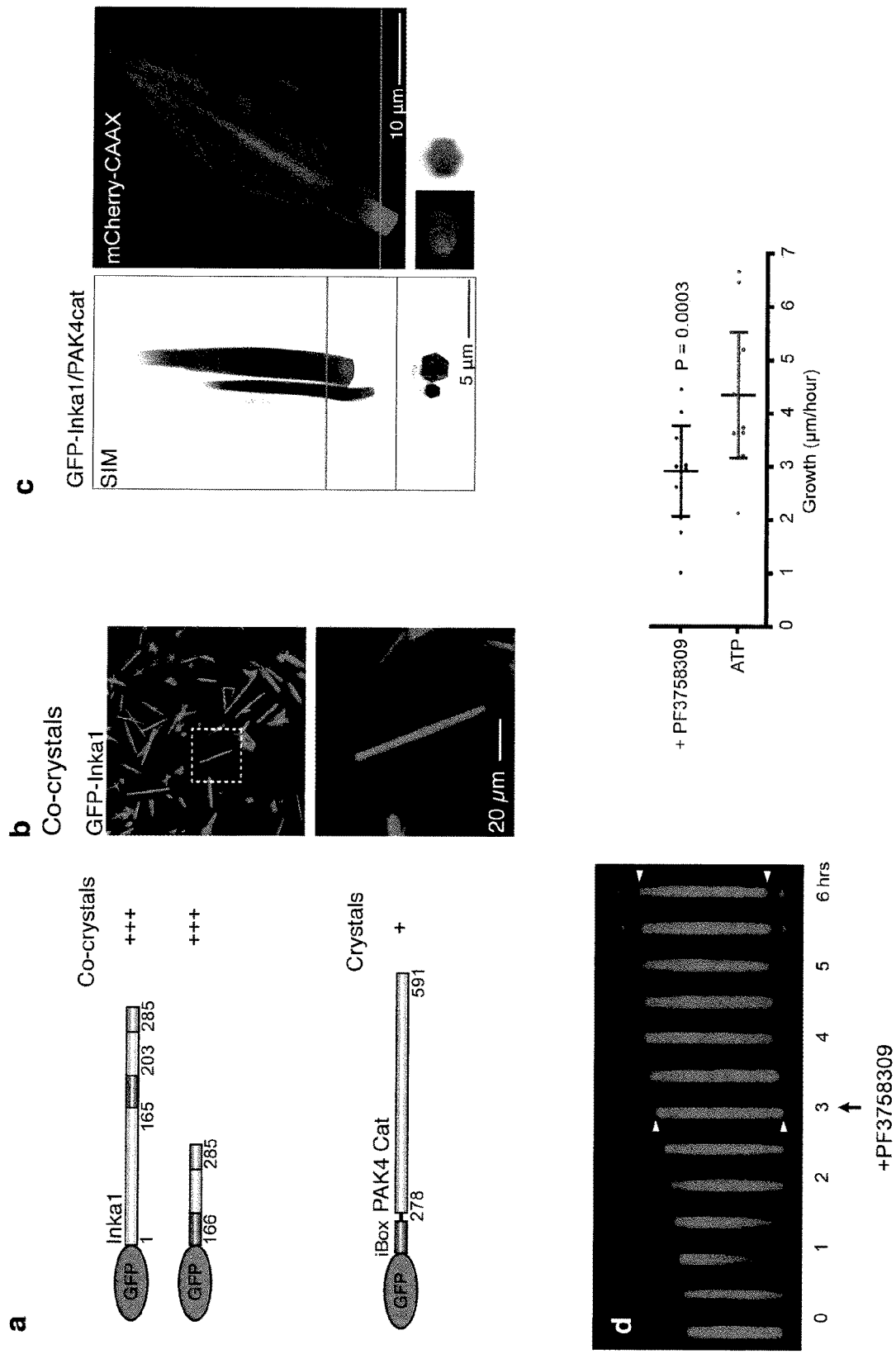

FIG. 6. Incorporation of GFP into PAK4 crystals and their in vivo dynamics (a) Schematic of the fluorescent Inka1 constructs generated and (b) the resultant in cellulo crystals when transfected with PAK4cat. (c) Structured illumination microscopy of a cell containing two crystals (SIM, left) and a single crystal observed by two channel confocal (right) images of GFP-Inka1:PAK4cat crystals. The cross sections (line) show the crystal enveloped by membrane. (d) Effect of addition of PF3758309 (5 μM, arrow) on a growing GFP-Inka1:Flag-PAK4cat crystal. GFP incorporation appears to occur at both ends based on the obvious depletion of GFP signal in the growing crystal after PF3758309 is added. The recovery of signal at 1.5 h after drug addition may be due to drug depletion. Right: The measured growth rates of GFP-Inka1 crystals before and after drug addition (n=17, error bars indicate 1 SD).

Figure 7:
Figure 7:
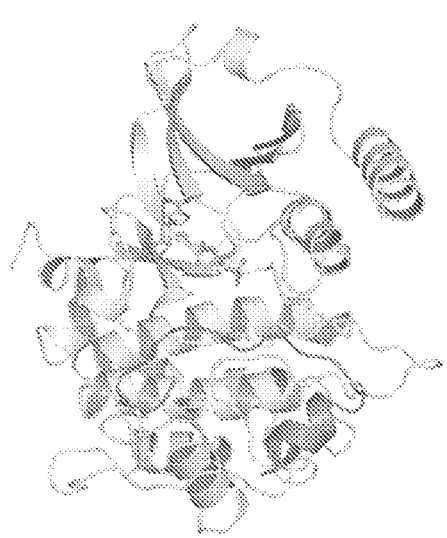
Figure 7:
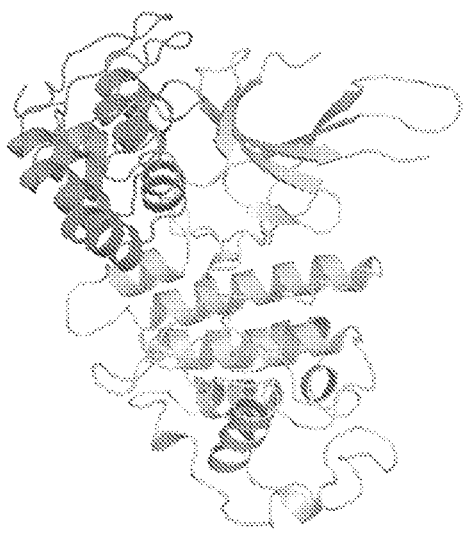
Figure 7:
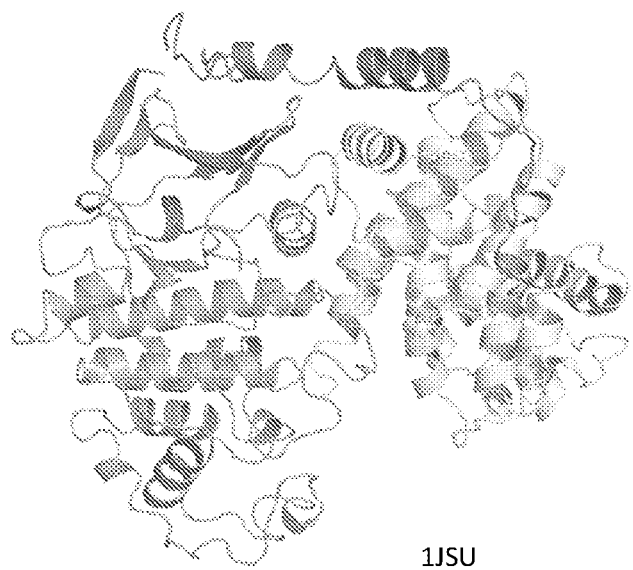

FIG. 7. Representative structures of complexes between known classes of endogenous inhibitors and their target protein kinases.

The orientation of the kinase domain (blue or green) in each case is positioned using the conserved secondary helices of the C-lobe. The organization of the inhibitor in each case is shown in red. In the case of p27 KIP, the cyclin A subunit (shown in yellow) provides an important helix to stabilize the CDK2 in an active state. Note that the PKI and Inka1 extended region take up similar positions between the N- and C-lobes, although the helical region of each contacts very different regions of the C-lobe.

Figure 8:
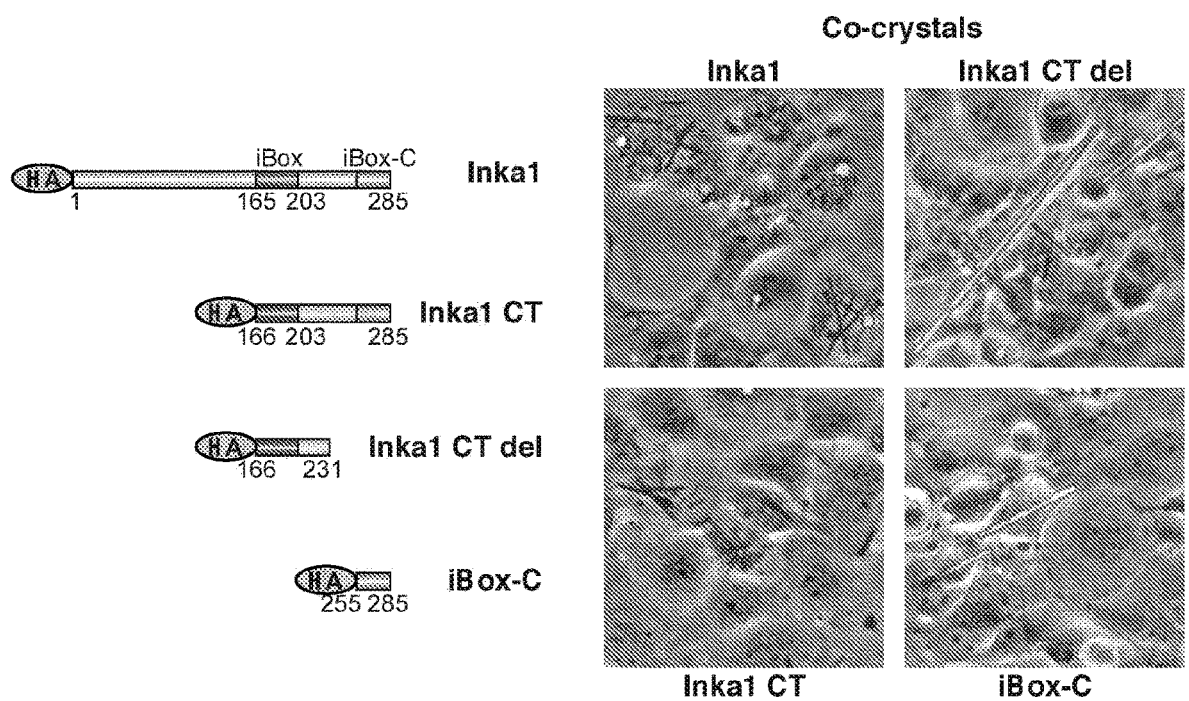

FIG. 8 Phase contrast images of PAK4 crystals in mammalian cells. Typical fields of COS7 cells viewed by phase-contrast microscopy (×10 objective) 48 h after transfection of full-length HA-Inka1 (or deletions thereof, as indicated) and co-expressed with Flag-PAK4cat.

Figure 9:
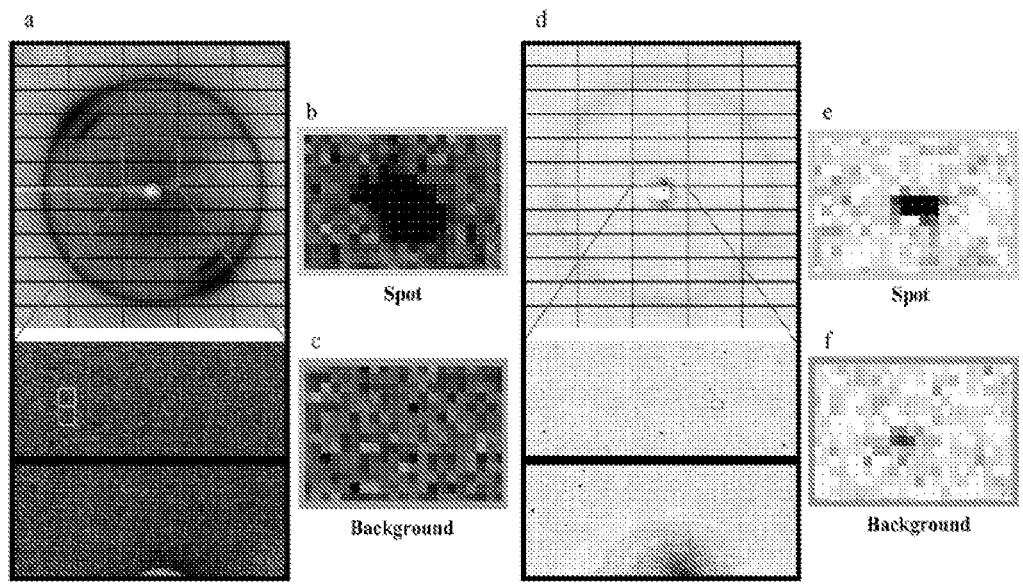

FIG. 9 Typical diffraction data from in vivo crystals. Representative diffraction pattern of an in cellulo crystal using full beam exposure versus that with the micro-apertures. Note the relative background signal in the left image. (a) The full beam diffraction image with a zoomed region indicating a spot (green box) or background (blue box). (b) A magnified view of the spot in the green box, revealing a low signal to background signal in the image. (c) A magnified view of the background in the image. (d-f) Similar views to those presented as A-C but with micro-apertures.

Figure 10:
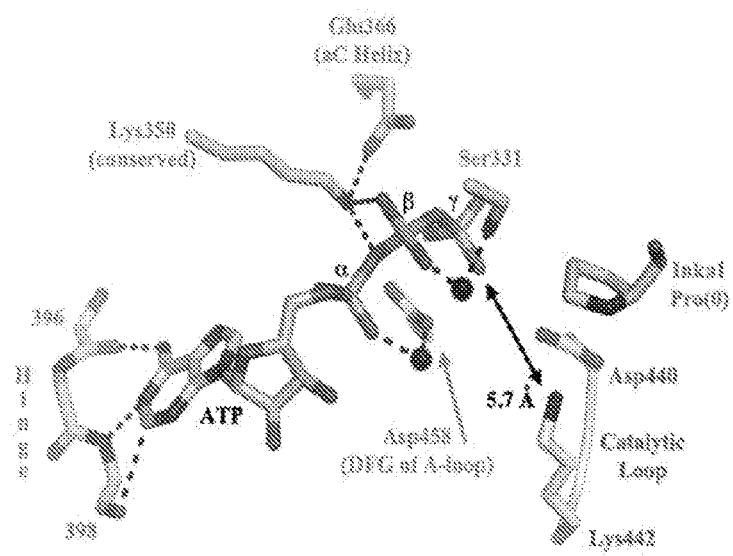

FIG. 10 The ATP-bound active site of PAK4:Inka1. Lys442 from the catalytic loop is relatively distant (5.7 Å) to the ATP γ-phosphate in the Inka1 bound structure. PAK4 residues are shown in cyan and yellow.

Figure 11:
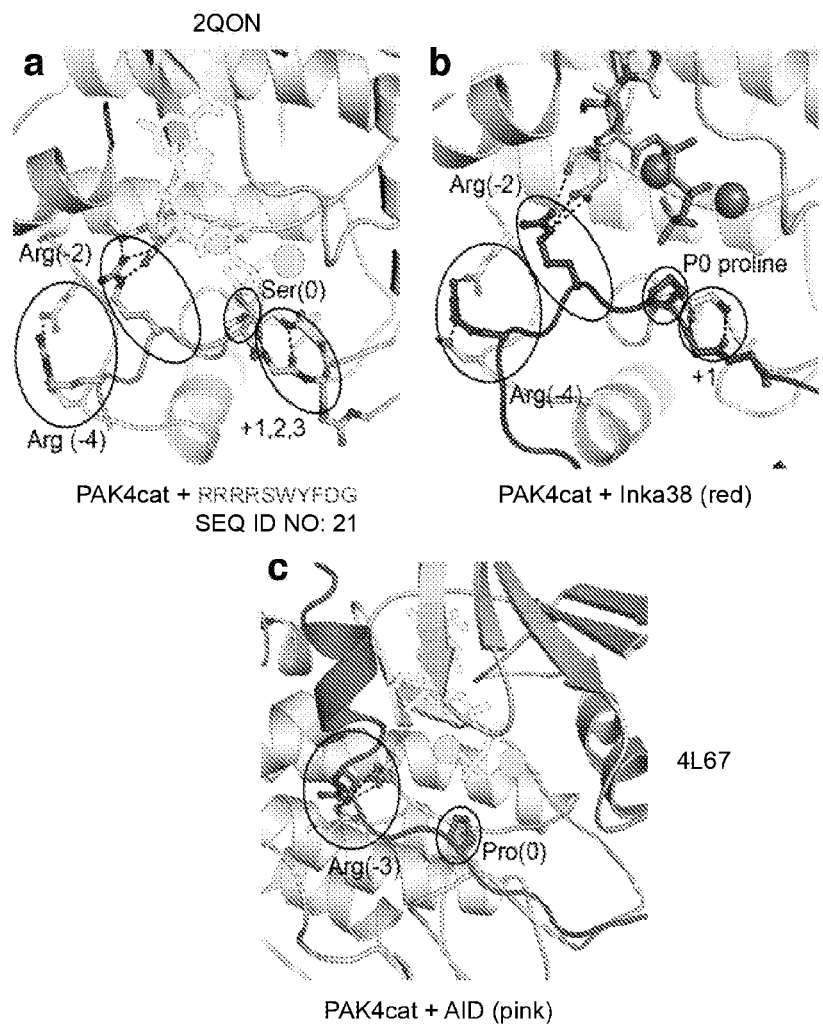

FIG. 11 The mode of Inka1 binding to PAK4cat resembles a pseudosubstrate interaction. Structural alignment showing the key PAK4 residues involved in substrate/inhibitor binding (a) A consensus substrate peptide RRRRRSWYFDG (SEQ ID NO: 13) bound to PAK4cat illustrates how specific acidic pockets accommodate the side-chains of Arg (−2) and Arg (−4). (b) Binding interactions of iBox of the Inka1 more closely resembles substrate binding than the auto-inhibitor (AID) of PAK4 (c) The side-chain interaction of the AID Arg (−3) relative to proline occurs in the acidic pocket occupied by Inka1 Arg (−2) but does not contact the Arg (−4) pocket. The positions of key contacts are circled.

Figure 12:
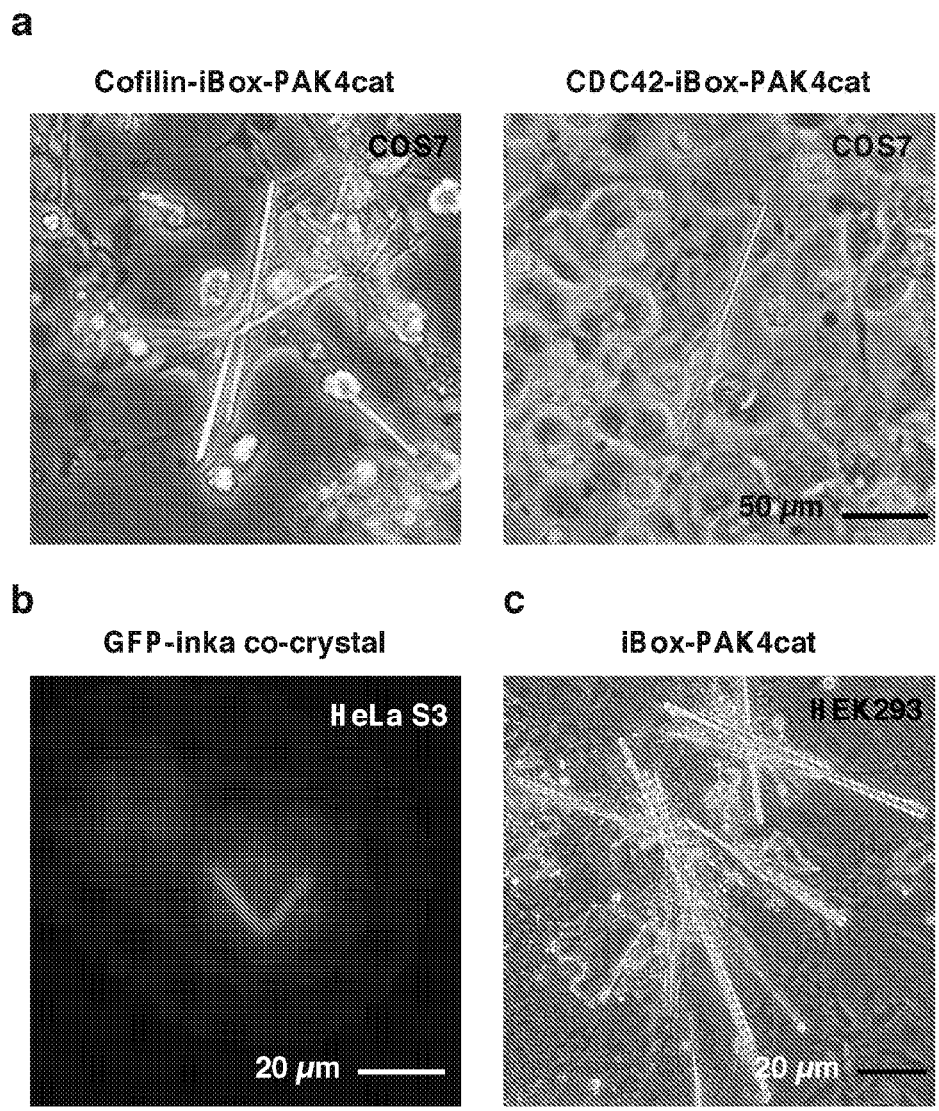

FIG. 12 Typical in cellulo crystals generated in different mammalian cell types. (a) The micrographs show the appearance of crystals formed 48 h after COS7 cells were transfected by plasmid encoding Cofilin (114D)-iBox-PAK4cat or Cdc42 (G12V)-iBox-PAK4cat fusions as indicated. (b) HeLaS3 were grown in suspension and transfected with plasmid encoding GFP-Inka1 and HA-PAK4cat. (c) HEK293 cells express and generate FLAG-iBOX-PAK4cat crystals utilizing a viral (Sendai) protein transfection system.

Figure 13:
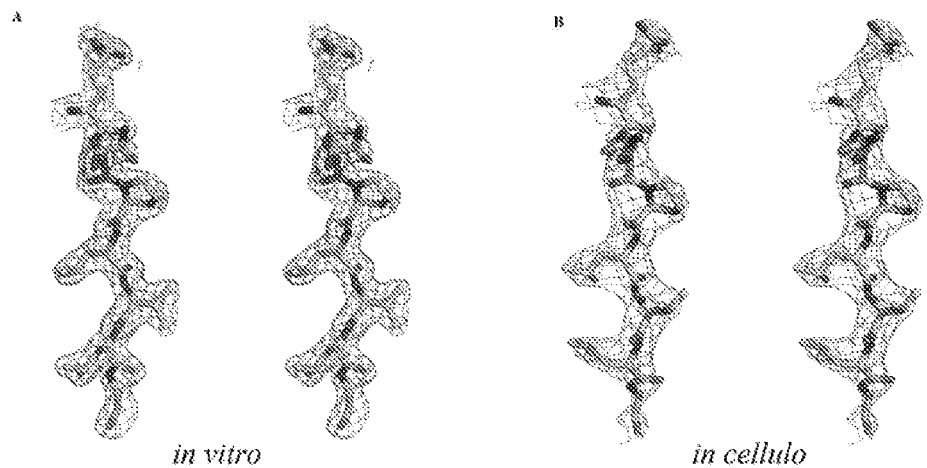

FIG. 13 Stereo images of portions of the 2Fo-Fc electron density maps contoured at 1.5 sigma and centered at P(0) in Inka. (a) in vitro (b) in cellulo.

EXAMPLE

1. Material and Methods

Cloning and Constructs.

All plasmid constructs were generated by PCR-based DNA amplification and inserts completely sequenced. The mammalian pXJ40-based vector with Flag, HA and GFP fusion tags are contain a standard CMV-derived promoter and β-globin 5' intron sequence. Inka1 constructs were cloned in pXJ-HA (as indicated in FIGS. 1 and 2) or pXJ-GFP (FIG. 6), while PAK1 and PAK4 were cloned in pXJ-Flag. Flag-GFP-iBox-PAK4cat comprised of residues 166-203 of human FAM212A (Inka1), a two-residue linker (Glu-Phe=EcoRI site), and the kinase catalytic domain of human PAK4 (278-591). For bacterial expression, pGEX4T1 (GE), pET28a (Novagen) and pSY5 (His tagged) were used as expression vectors for Inka1 (166-203), PAK1 (1-545) and PAK4 (286-591), respectively. The 13-residue peptide PAK substrate Raf1(S338) PRGQRDSSYYWEI (SEQ ID NO: 14) (Raf13p) was as previously described 1.

Expression and Purification of Recombinant Proteins.

Recombinant proteins were expressed in *Escherichia coli* BL21-CodonPlus(DE3) (Stratagene) grown at 30° C. The bacteria were grown to an optical density of 0.6 (OD 600 nm) before induction with 1.0 mM IPTG. Induction was carried out for 3 hours at RT, or 16 hours at 4° C. Bacterial lysates were purified with GSH-Sepharose (GE) or nickel Ni-NTA-Agarose (Qiagen) columns to extract the overexpressed proteins. The recombinant proteins were eluted in 50 mM Tris-HCl, pH 8.0, 150 mM NaCl, 0.5% Triton X-100, 10% glycerol with 5 mM glutathione (for GST fusions) or 250 mM imidazole (for poly-histidine tagged proteins). With PAK kinases the elution buffer was supplemented with 1 mM $MgCl_2$. Proteins were diluted and snap frozen in aliquots prior to use. SDS-PAGE and Coomassie Brilliant Blue staining assessed protein purity to be greater than 90%.

Cell Culture, Transfection and Immunoprecipitation.

Monkey COS-7 cells, human HEK293 and U2OS were grown in Dulbecco's modified Eagle's medium (DMEM) with 4500 mg/l glucose supplemented with 10% bovine calf serum (Hyclone). HeLa cells were grown in Eagle's minimal essential medium (MEM), supplemented with L-glutamine, sodium bicarbonate, sodium pyruvate and 10% bovine calf-serum. Transient transfections were performed with Lipofectamine 2000 according to recommended protocols. Typically, a total of 5 µg plasmid DNA was used per 60 mm dish; lysates were harvested 18 h later in ice cold lysis buffer (0.5 ml; 25 mM HEPES pH 7.3, 100 mM KCl, 5 mM $MgCl_2$, 20 mM β-glycerophosphate, 5% glycerol, 0.5% Triton-X100, 5 mM DTT, 0.5 mM PMSF, 1 mM $Na_3VO_4$ and x1 protease inhibitor cocktail (Roche)). To test co-immuno-precipitation of proteins, the lysates were clarified by centrifugation (14,000 g) and the clarified lysates were incubated while rolling (2 h) with 20 µl M2 anti-Flag Sepharose (Sigma-Aldrich, A2220). Rabbit anti-Flag (Sigma-Aldrich, F7425) or HRP coupled anti-HA (Santa Cruz Biotechnology, sc-7392 HRP, 1 µg/ml) were used for Western analysis.

In Vitro Kinase Assays.

Purified PAK1 or PAK4 (50 nM in 25-50 µl) were incubated with 10 µM GST-Raf1S338 peptide in 10 µM ATP (2 µCi of γ32P ATP) of kinase buffer (25 mM Hepes, pH 7.3, 0.1% Triton-X100, 50 mM KCl, 10 mM $MgCl_2$, 1 mM DTT) at 30° C. for 20 min. Samples were analysed by SDS-polyacrylamide gel electrophoresis, or adsorption of the GST substrate mix onto PVDF membranes, followed by extensive washing to remove free γ32P-ATP. The synthetic peptides of 95% purity, as determined by HPLC and MS analyses (GenScript), were soluble in aqueous PBS. Stock solutions (10 mM) were quantified via calculated extinction coefficients and absorbance measurements at 280 nm and stored at −80° C. The diluted peptides were incubated at the indicated concentrations with the kinase on ice (10 min) before addition of γ32P ATP and subsequent incubation at 30° C. The synthetic peptide array (Jerini Biotools) was phosphorylated in situ as described previously.

Generation and Harvesting of Intracellular PAK4 Crystals.

COS-7, HeLa, HEK293 or U2OS cells (35 mm culture dish or glass cover-slip) were typically transfected with 2.5 µg of each plasmid in 2 ml of media using Lipofectamine 2000 (Invitrogen) or the GenomeONE™ Neo EX haemagglutinating virus of Japan envelope (HVJ-E) transfection kit (Cosmo Bio Co Ltd) under the manufactures' recommended conditions. Crystals were observed by phase contrast microscopy using a ×10 objective (Nikon Eclipse TE300) 1-4 days post transfection. The structure of Flag-iBox-PAK4cat (FIGS. 2 and 3) was determined from crystals grown in COS-7 cells. The cells were harvested 3 days after transfection by incubating in PBS with 0.125% (w/v) trypsin and 25% (v/v) glycerol (Merck) for 30 minutes. Individual cells containing single crystals were then mounted in 0.1-0.2 mm cryoloops (Hampton Research) and flash-cooled in liquid nitrogen.

In Cellulo X-Ray Data Collection and Structure Determination.

A 2.95 Å data set was collected at the microfocus beamline I24 of the Diamond Light Source equipped with microapertures, limiting the beam cross sectional area to 6 µm×6 µm, at wavelength of 0.9686 Å with a PILATUS3 6M detector (DECTRIS, Baden, Switzerland) by merging the diffraction data from five isomorphous crystals. The data were processed with xia2 and the structure solved by molecular replacement with Phaser, using the coordinates of the catalytic domain of human PAK4 (PDB 4FIE) as the search model. The solution was then built in COOT, refined to completion using REFMAC5 [64] and validated via the MolProbity web server. Structure figures were generated using PyMOL (The PyMOL Molecular Graphics System, Version 1.3 Schrödinger, LLC). The atomic coordinates and structure factors have been deposited in the Protein Data Bank (PDB 4XBU).

In Vitro Crystallization, X-Ray Data Collection.

6His-PAK4cat protein was purified under standard conditions using a semi-automated Akta system [11]. The crystallization of 6His-PAK4cat was carried by hanging drop at 5 mg/ml with 15 fold molar excess of the iBox 23mer synthetic peptide, AEDWTAALLNRGRSRQPLVLGDW (SEQ ID NO: 15), and two times molar excess of ATP. Bipyramidal-shaped crystals grew in 0.1 M Tris-HCl, pH 8.5, 12% PEG 8,000 at 25° C. Crystals were supplemented by 15% glycerol and flash-cooled in liquid nitrogen. X-ray data were collected at wavelength of 0.9686 Å on I24 of the Diamond Light Source and structure solution and refinement carried out as documented for the in cellulo crystals.

Live Cell Imaging of Crystal Growth, Fixed Sample SIM and Confocal Analysis.

The cells were plated at 50% confluence glass cover slips overnight: plasmid transfection used GFP-iBox-Pak4cat and FLAG-iBox-Pak4cat constructs at a ratio of 4:1 to promote crystal nucleation. The cover slips were transferred to a Chamlide magnetic chamber (Live cell instruments, Seoul, Korea) with 5% $CO_2$ at 37° C. for live imaging on an Zeiss Axiovert 200M Live Cell Imaging with a 10× objective. We imaged multiple chosen regions for 8 hours at 6 min intervals. To measure crystal growth rate, we used instead a Nikon Eclipse Ti microscope equipped with spinning disk confocal attachment (Yokogawa CSU-22 module) to avoid photo-damage. The cells were imaged at 60×1.4 NA objective at 2 min intervals. For SIM and confocal imaging, cells were fixed in non-hardening mounting media (Vectashield). The slides were imaged by Delta vision OMX SIM with a 100×1.4 NA objective. Confocal imaging used an Olympus FV1000 upright system with 60×1.42NA objective. The 3D stacks were analyzed by IMARIS software.

2. Results

Inka1 is an endogenous PAK4 Inhibitor.

We previously reported that the Cdc42 effector PAK4 is regulated by an auto-inhibitory domain (AID, FIG. 1A), which serves to control the constitutively phosphorylated catalytic (PAK4cat) domain [1]. Although Cdc42 up-regulates PAK4 activity in vivo this kinase activation cannot be observed using recombinant proteins in vitro [2], indicating other protein(s) might be involved. Indeed it has been suggested that Src SH3 domain interaction with the core AID sequence might be an alternate means of regulating PAK4 [2], although a cellular Src-PAK4 interaction has not been detected. There are few PAK4-interacting proteins known other than the Cdc42-like GTPases. One *Xenopus* PAK4 binding protein originally identified through a yeast two-hybrid screen is a 30 kDa neural crest enriched protein termed Inka1 [previously Inca [8,9]], although the role of this putative adaptor was not determined. The protein is also designated FAM212a and FAM212b in the protein database based on their common central 38 amino acid sequence (166-203) here termed the Inka box (iBox, FIG. 1a).

We decided to investigate the role of human Inka1 by further testing its ability to bind to various PAK4 constructs in mammalian cells. Inka1 bound to an activated PAK4 with a mutated AID (designated PAK4*) significantly better than wild type PAK4 (FIG. 1b). This suggested that the PAK4 AID limits Inka1 access to the PAK4 catalytic domain (FIG. 1b) with which it interacts (Luo et al, 2005). The recombinant 38 amino acid 'Inka box' (GST-iBox) is a potent of PAK4cat inhibitor in vitro (FIG. 1c) but does not affect PAK1, suggesting Inka1 is a specific group II PAK inhibitor. Inka1 likely acts also on PAK5 and PAK6 since their substrate binding pockets are essentially identical. In vitro measurements indicate GST-Inka1 has a Ki of 30 nM (FIG. 1d), which is comparable with the avidity of PKI for PKA. The iBox sequence (FIG. 1a) contains the tripeptide PLV in common with the PAK4-AID, which binds in the substrate-docking site [2,10].

Inka1 has Two Functional Inhibitory Regions

Intriguingly we noted that the inhibitory iBox appears to be duplicated in the C-terminal 22 amino acids of Inka1 (FIG. 1a and FIG. 2c), which we term iBox-C. Synthetic 24mer peptides, corresponding to the N- or C-terminal ⅔rd of the iBox or the iBox-C, exhibited Ki values of 0.2-0.4 µM (FIG. 1d) which suggested that all 38 amino acids centered on the PLV motif are involved in PAK4 inhibition. Thus Inka1 functions as an Inhibitor of kinase activity; given that it lacks sequence conservation outside these PAK4 inhibitory motifs (the iBox or iBox-C) it seems likely the main function of the protein is to negatively regulate PAK4 activity. Deletion of either Inka1 or Inka2 cause subtle defects in frog and mouse development [8,9], not inconsistent with human Inka1 being causative in a chromosomal microdeletion being associated with cleft lip and CNS abnormalities. Inka1 is expressed in a number of cell types in the early mouse embryo[8].

Inka1 Forms Crystals with PAK4 in Cells.

We asked whether Inka1 and PAK4 co-localize in mammalian cells (FIG. 2a). Inka1 alone is predominantly nuclear but PAK4 is not. However co-expressing PAK4, which has been reported to contain an N-terminal nuclear localization signal, redistributed Inka1 into the cytoplasm. This is interesting given the established role of PKI in terminating nuclear but not cytoplasmic PKA signals. We next tested whether Inka1 inhibits active PAK4cat in vivo. Unexpectedly the co-expression of these proteins consistently yielded cytoplasmic protein crystals that contained both Inka1 and PAK4, judged by immuno-staining (FIG. 2b). By phase contrast microscopy these often appear as single elongated crystals >50 µm that extend across the cytoplasm (FIG. 2b, boxed region). Curiously many truncated Inka1 constructs were capable of forming crystals with PAK4cat, when these contained either the central iBox or iBox-C(FIG. 2c). These crystals look remarkably similar (FIG. 8) suggesting they have the same underlying organization. Inka1 constructs that contain both copies of the PAK4 inhibitory regions (residues 165-285) were most efficient at inducing crystals. The C-terminal 31 amino acid of Inka1 (255-285) was able to induce crystals more efficiently than the Inka1 (166-203) when they are expressed as HA-tagged proteins although the iBox38 has a higher affinity in vitro. In order to confirm that these crystals indeed contain a 1:1 ratio of both components we generated a single chain Flag-iBox-PAK4cat construct as illustrated in FIG. 2c. This expression construct yielded abundant in cellulo crystals in multiple human cell types.

The in Cellulo Structure of Inka1 Bound to PAK4cat.

Since the crystals of PAK4 appeared to be relatively stable within the cell we decided not to attempt to purify these further. To tackle the in cellulo crystal structure of iBox-PAK4cat, intact monkey COS-7 cells that contained large single needle crystals (<5 µm in cross section by 50-100 µm) were trypsinized to yield rounded cells in which large crystals could be easily observed (FIG. 2d arrows). The cells containing the largest crystals were individually mounted in cryoloops and flash frozen (FIG. 2e). These crystals were exposed to X-rays on the Diamond synchrotron microfocus beamline 124 equipped with microapertures. Typical diffraction data are given in FIG. 9, which illustrate the importance of this micro beam to the quality of data. The merged data from five crystals led to the structure being solved at 2.95 Å resolution (FIG. 3a); the statistics for which are given in Table 1 below. To our knowledge, this is the first in cellulo crystal structure of a mammalian protein to be elucidated within intact mammalian cells.

TABLE 1

Statistics of data collection and refinement

|  | In cellulo PAK4cat:iBox | In vitro PAK4cat:iBox |
|---|---|---|
| Data collection |  |  |
| PDB Code | 4XBR | 4XBU |
| Space group | P6$_3$ | P4$_1$2$_1$2 |
| Unit cell dimensions (a, b, c) (Å) | a = b = 144.0, c = 62.5 | a = b = 65.2, c = 184.2 |
| (α, β, γ) (°) | α = 90, β = 120, γ = 90 | α = 90, β = 90, γ = 90 |

TABLE 1-continued

Statistics of data collection and refinement

|  | In cellulo PAK4cat:iBox | In vitro PAK4cat:iBox |
|---|---|---|
| Resolution (Å) | 44.2-2.94 (3.02-2.94) | 29.3-2.06 (2.11-2.02) |
| $R_{merge}$ (%) | 29.4 (60.0) | 7.4 (75.4) |
| Average I/Iσ (%) | 10.9 (2.2) | 21.2 (3.9) |
| Unique reflections | 15517 | 25890 |
| Completeness (%) | 97.3 (83.4) | 100.0 (99.9) |
| Redundancy | 7.8 (2.0) | 12.8 (12.6) |
| Refinement |  |  |
| Resolution (Å) (highest resolution shell) | 20.0-2.94 (3.02-2.94) | 20.0-2.06 (2.11-2.06) |
| No. of reflections: working/test | 14702/776 (906/44) | 24541/1262 (1599/79) |
| $R_{work}/R_{free}$ | 18.9/23.0 (32.1/39.3) | 21.1/24.7 (25.8/34.3) |
| No. of atoms: | 2536 | 2472 |
| Residues PAK4/iBox | 297-589/175-197 | 297-589/178-189 |
| RMSD bond length (Å) | 0.008 | 0.013 |
| RMSD bond angle (°) | 1.50 | 1.60 |
| Mean B-factor (Å$^2$) |  |  |
| PAK4/iBox | 68.9/108.9 | 38.6/50.3 |
| Water | — | 44.0 |
| ATP/Mg$^{2+}$ | 90.2/54.0 | —/— |
| Ramachandran (%) favoured/allowed/general/disallowed | 86.1/13.6/0.4/0 | 92.0/8.0/0/0 |

The X-ray structure of these in cellulo crystals provided us with a number of important insights: under cellular conditions PAK4cat adopts a typical 'closed' active kinase conformation that includes ATP bound to two magnesium ions. As we expected, the activation (A) loop Ser474 is phosphorylated, and the central region of the iBox is packed against the kinase through both main chain and side chain interactions (FIG. 3a). The side chain of PAK4 Arg359, which lies at the end of the αC helix, stabilizes the catalytic competent state by interacting with the phospho-Ser474. When the N-lobe αC helix is held in such a 'closed' state with respect to the C-lobe, it allows for proper coordination of bound ATP.2Mg$^{2+}$ for catalytic transfer. Most structures with or without substrates bound show a coupling between Arg359 and the Ser474 phosphate: the phosphorylated PAK1 Thr423 appears to use the same A-loop to phosphate coupling to stabilize the αC helix in an active state. Indeed such coupling may well be common mechanism feature of kinases in which activation loop phosphorylation is essential for activity, for example PKA.

On the basis of these experiments, we hypothesize that Inka1 stabilizes the ATP-bound crystallization-competent conformation of the kinase domain by preventing ATP hydrolysis through binding tightly in the cleft between the N- and C-lobes. This in cellulo iBox-PAK4cat structure determined in space group P6$_3$ was verified by comparison with the structure of the complex determined at 2.0 Å resolution from P4$_1$2$_1$2 crystals grown in vitro from purified PAK4cat and a synthetic iBox 24mer peptide (FIG. 3b). These two structures are essentially identical, although more of the Inka1 backbone is visible in the in cellulo structure and in vitro structure lacks bound ATP and Mg$^{2+}$. We are able to determine the side chain disposition of 28 of the 38 iBox amino acids; the relative close disposition of the visible N- and C-termini suggest the remaining residues make intra-molecular contacts to stabilize the Inka1 inhibitor in a loop like manner. This hypothesis is consistent with the relative Ki of the various Inka1 peptides shown in FIG. 1.

The main chain and side chains of Inka1 residues 171-196 are clearly visible with the C-terminal F191-N197 forming a helix that packs against the C-lobe (FIG. 3b). This interaction primarily involves the packing of hydrophobic side chains of Inka1 including F191, L194 and V195 against the end of the C-lobe helix α-EF and Arg488. It is likely that these interactions provide kinase specificity since this region is in general more diverse. Interestingly this part of the PAK1 C-lobe including both helix α-EF and α-G makes extensive contacts with its auto-inhibitory domain, which can inhibit Pak1 with 20 nM affinity (in trans). Unlike Inka1, the PAK1 AID makes no contacts with the substrate binding pocket (it is not a pseudo-substrate), but it does displace the A-loop to prevent the catalytic domain adopting an active state.

The disposition of the core Inka1 sequence (RSRQPLV-LGD) (SEQ ID NO: 16) in the current structure shows docking in to the substrate binding pocket (primarily via R-2 and R-4 interactions, FIG. 4c) and the inhibitor chain runs parallel to, and hydrogen bonds with, several main chain residues of the activation loop in a beta sheet-like manner (FIG. 3a). Comparison of the PAK4-bound iBox structure (FIGS. 3a and b) with that of the PAK4 AID PAK4 (Wang et al, 2013) reveals a common geometry underlying the inhibition. The iBox and AID core sequences resemble a bound consensus substrate peptide, however the iBox and AID contain a proline residue in place of target serine designated Ser(0). Analysis of the bond angles of these residues reveals that they fall in the same region of the Ramachandran plot (FIG. 3c). It seems the relative rigidity of proline stabilizes the favorable PAK4-binding conformation of the iBox and AID peptides that mimic bound serine, thus explaining why proline was selected in both during evolution. This is different to most other intramolecular kinase pseudo-substrate sequences, for example those in the large protein kinase C family in which the alanine is present in place of Ser(0) (RRGA(0)IKQ) (SEQ ID NO: 17) in PKCα. For the well-known PKA inhibitors or PKIs, an alanine occupies the Ser(0) and again basic residues at the −2 and −3 positions are critical for kinase domain interaction in the substrate-binding pocket (RRNA(0)IHD) (SEQ ID NO: 18) in PKIα. The AID and Inka1 structures similarly feature Arg-mediated salt bridges that bind an acidic pocket, and hydrophobic side chain interactions at the +2 and +3 positions.

Inka1 Binds to PAK4 in a Substrate-Like Manner

Inspection of the three structures (FIG. 4a) suggests a mechanism of phosphate transfer, similar to that proposed for the PKA and other protein kinases, with PAK4 Lys442 and Asp440 from the catalytic loop, being close to the ATP γ-phosphate and Inka1 Pro(0), respectively (FIG. 10). To test the model that these inhibitory sequences closely mimic substrate binding (FIG. 11), we replaced Pro(0) with Ser, and tested the synthetic 13mer peptides as PAK4 substrates in situ (FIG. 4b). The AID-based peptide was phosphorylated as efficiently as Raf1 Ser338 [1], but Inka1-derived sequences were significantly better substrates. Alanine scanning substitution showed that the presence of AID Arg(−3) or Inka1 Arg(−2) were critical for peptide phosphorylation. These side chain contacts of Inka1 arginines (FIG. 4c) involve two acidic substrate binding pocket (circled in FIG. 11). Based on the phosphorylation profile both the iBox and iBox-C Arg(−4) sidechains contribute significantly to peptide binding. In the PAK4:Inka1 structure the hydroxyl of the Inka1 Ser(−3) side chain forms a hydrogen bond with the Inka1 main chain; however only in the iBox-C did we note a significant loss of interaction following Ser(−3)Ala substitution. Changing the iBox Leu(+1) and Leu (+3), which lie on a hydrophobic shoulder of the kinase, to alanine affected phosphorylation (FIG. 4b,c) as a result of reducing the side chain hydrophobicity. Together these observations explain the conservation of the RSRQPIvI (SEQ ID NO: 19) motif among the iBox sequences (FIG. 1, upper case invariant; lower case positions non-bulky hydrophobic residues).

The Kinase-Kinase Contacts in Inka1:PAK4 Crystals

Inspection of the crystal packing revealed that the crystal is formed by only two types of contacts, both of which are between PAK4cat units (FIG. 5). The crystal packing resembles that obtained for a short (346 residue) isoform of full-length PAK4 [2] in which the N-terminal regulatory region is largely disordered, excepting the pseudosubstrate like peptide (4FIG). In the in cellulo crystals one set of crystal contacts is formed by the interaction between neighboring N-lobes that involves the two helices from one N-lobe interacting with the 3-sheet of the adjacent N-lobe, an interaction area of 768 Å$^2$. The N-lobe interactions form strands that run the length of the crystal (FIG. 5b). The hexagonal packing requires that the N-lobe to be in a 'closed' state relative to the C-lobe, which is likely achieved through 'clamping' of the Inka1 inhibitory region. Interestingly the PAK5cat sequence is slightly different at this interface, and thus does not generate in cellulo crystals with Inka1. The second set of contacts lies at the 3-fold axis mediated by the PAK4cat C-lobes involving primarily hydrophobic residues; each C-lobe contributes 576 Å$^2$ to this crystal contact (FIG. 5c). Remarkably the iBox is not involved in crystal contacts and is exposed to the large 80 Å diameter central solvent channels that run the length of the crystals (FIG. 5a). These observations thus explain the ability of multiple Inka1 deletion constructs to form crystals with PAK4, since there exists a large space to accommodate the various polypeptides associated with either iBox or iBox-C.

The packing between the N-lobes, as observed in the in cellulo P6$_3$ crystal form, is also reproduced in the in vitro P4$_1$2$_1$2 crystal reported here and elsewhere [2, 11-13] and in an in vitro P2$_1$2$_1$2$_1$ crystal [14, 15] demonstrating that this interaction is conducive for crystallization. These two crystal forms support a range of apo peptide inhibitors and small molecule inhibitor complexes with PAK4cat. Furthermore, both the in cellulo P6$_3$ three-fold and N-lobe packing interactions are observed in the in vitro P3 structures of PAK4 full length, PAK4cat and PAK4cat with bound peptide RPKPLVDP [2](SEQ ID NO: 20). Thus, the two molecules in the asymmetric unit of the P3 parent crystals possess the central channel and share similar packing to the single molecule in the asymmetric unit of the in cellulo P6$_3$ crystals. Both P3 and P6$_3$ crystals are able to accommodate larger constructs beyond the PAKcat domain that forms the entire crystal packing, namely the N-terminus of PAK4 and Inka1 sequences, respectively.

In addition to the above, the present invention includes any mutation to the protein sequences of the kinase and its inhibitor. For example, mutation of the PAK4 sequence such that amino-acid changes at the kinase-kinase interface may increase (a) the stability of the crystal lattice, or (b) increases or alters the properties of the crystallization in cells or in vitro. For example, the residues that may be mutated are shown in FIG. 5 (for example mutations of L422 to F or A307 to V), which increase the extent of the hydrophobic interface between the C-lobe or the N-lobe interfaces— without disrupting the protein crystal structure.

High Resolution Imaging of Crystal Formation

Based on the crystal structure described above and the available space in the lattice, we postulated that hybrid proteins of up to 30 kDa when fused to the iBox might also co-crystallize with PAK4cat in cellulo. Indeed several GFP-Inka1 constructs readily formed co-crystals with PAK4cat (FIG. 6) when expressed in mammalian cells. The crystals formed with GFP-Inka1 and Flag-PAK4cat, allowed for time-lapse analysis of crystal formation. By expressing the membrane marker RFP-CAAX, the plasma membrane could be observed to surround the crystal as it exceeds the normal dimensions of the cell. The co-crystallization of GFP-Inka1 and PAK4cat was modeled to demonstrate that there is sufficient scope in the PAK4cat packing to accommodate GFP. At this stage we are unable to confirm that the GFP itself is ordered sufficiently to obtain high resolution diffraction data. Super-resolution (SIM) imaging of these GFP crystals revealed their underlying hexagonal symmetry (FIG. 6c).

Since the Flag-iBox-PAK4 crystal structure contained bound ATP, which is stabilized by the Inka1 inhibitory peptide (FIG. 3a), we were interested on the effect of the ATP-competitive PAK4 inhibitor PF-03758309, which binds with 10 nM affinity in vitro [14]. Unexpectedly, GFP-Inka1: HA-PAK4cat co-crystals reproducibly became depleted of GFP signal during the elongation phase in 5 μM PF-03758309 (FIG. 6d). Thus PF-03758309 appears to allow PAK4cat to incorporate with sub-stoichiometric levels of GFP-Inka1, consistent PF-03758309 either reducing the affinity of GFP-Inka1 or allowing PAK4cat incorporation without Inka1. The average crystal growth along the length (FIG. 6d) was 4.2+/−1.2 μm/hour, which equates to adding a new layer of crystal lattice every three seconds comprised of ~50,000 protein units (for a crystal with 2 μm cross section). Crystal growth slowed after PF3758309 addition. Based on this analysis we observed PAK4cat incorporated at both ends of the crystal (FIG. 6d).

3. Discussion

The formation of crystals or filaments in mammalian cells is unusual but not unprecedented. Depletion of ATP in cells leads to the assembly of cofilin-actin rods in various cell types including neurons, and these rods can be purified. The enzyme CTP synthase dynamically assembles into macromolecular filaments in bacteria, yeast, *Drosophila*, and mammalian cells; it has recently been shown this might be a physiological response regulated by the non-receptor Cdc42-effector kinase DAck in the *Drosophila* embryo. In these two cases there is evidence that the assemblies play functional role which has been conserved. It should be noted that PAK4 only forms crystals when it is truncated, and one would anticipate such a propensity (in full-length proteins) would be selected against during evolution.

Many human protein kinases are negatively regulated via interaction of the catalytic domain with an auto-inhibitory domain or AID, but a few are also targeted by (small) inhibitory proteins, which provide an additional layer of regulation. We have identified Inka1 as a potent vertebrate inhibitor of PAK4 with a Ki of ~30 nM (FIG. 1), which has a much higher affinity than the corresponding AID. Inka1 contains two copies of the kinase inhibitory domain, and both of these small regions of themselves can support PAK4cat crystal formation in cells (FIG. 4). To our knowledge, Inka represents one of only six classes of established endogenous protein kinase inhibitors to be uncovered to date. It is likely that more remain to be found among the plethora of orphan open reading frames in the human genome, however none of these different proteins share sequence homology.

Among known endogenous kinase inhibitors, Inka1 represents one of four whose basis of inhibition is understood at the structural level. The three members of the PKA inhibitor family, termed PKIs, are proteins of <100 residues sharing an N-terminal region of 25 amino acids, which interact with the PKAc catalytic domain as illustrated in FIG. 7. There is evidence that PKIγ is required for export of PKA catalytic subunits from the nucleus back to the cytoplasm following activation of PKA in the brain. Based on sequence homology searches, PKI proteins can be found in many invertebrates (cf. K09E9.4 in *C. elegans*) but not in certain groups such as *Drosophila*. Two closely related $Ca^{2+}$ calmodulin-dependent protein kinase II inhibitors (CaM-KIIN) of 78 and 79 amino acids have been characterized, and show ~50 nM Ki in vitro.

The best-studied endogenous inhibitors are cyclin-dependent kinase (CDK) inhibitors. The INK4 gene family encodes p16INK4a, p15INK4b, p18INK4c, and p19INK4d, all bind to CDK4 and CDK6 and block their association with D-type cyclins. The INK4 inhibitor structure is different from the others described here, in being well folded in the absence of kinase (FIG. 7). The Cip/Kip family members vary widely in size and comprise p21 Cip1/Waf1/Sdi1, p27Kip1, and p57Kip2. These share a conserved N-terminal domain that binds in an extended manner to both cyclins and CDKs, as illustrated in FIG. 7. These proteins, much like the JIP family of MAPK scaffold proteins, are not stand-alone kinase inhibitors, but rather form a modulatory platform essential for CDK signaling. Finally, the Raf1 and GRK2 inhibitor RKIP is extensively studied and its structure known, but the way by which this protein binds to kinase targets is not known. Mapping studies indicate the non-catalytic domain of Raf1 binds RKIP, which differentiates it from the protein kinase inhibitors shown in FIG. 7.

Both Inka1 and Inka2 are nuclear localized proteins (FIG. 2), which can be co-immunoprecipitated with Pak4, particularly when the kinase is in an open active state. Inka proteins share sequence homology only in the region that binds to PAK4, which was termed the Inca box, however we demonstrate that Inka1 (but not Inka2) contains two related functional PAK4 inhibitory modules. There has been some discussion regarding the role of PAK4 in the nucleus since the kinase undergoes nucleo-cytoplasmic shuttling. The Inka1-LacZ allele expression in mice indicates expression in the cephalic mesenchyme, heart, and paraxial mesoderm prior to E8.5. Subsequently, expression is observed in the migratory neural crest cells, however the majority of Inka1-/- mice are viable and fertile [8] pointing to compensation by Inka2. Thus at this point we infer that Inka1 plays a redundant role in regulating PAK4 activity, and may well be compensated by Inka2 in mice.

A coral fluorescent protein that forms diffraction-quality micron-sized crystals within mammalian cells is recently reported [6]. These crystals assemble much more quickly and likely recognized as foreign, since they are processed as autophagic cargos. By contrast our crystals form at a modest pace in the cellular context, and grow for 6-16 h suggesting they are well tolerated in the cytosol over this time period. The complex between PAK4 and Inka1 is the first human protein structure to be solved within mammalian cells, and further, multiple constructs of Inka1 or fusions to other proteins can be incorporated into the PAK4 crystal lattice (FIGS. 2 and 6). Crystals have been grown in a variety of mammalian cell types, monkey COS-7 and human HeLa and HEK293 (FIG. 12).

We note parallels to the small molecule "crystalline molecular flasks", which have allowed the X-ray structures of the guest molecules to be solved in host frameworks [7]. Stabilizing such guest proteins in a single state probably requires additional engineering of the channel surface, which is currently ongoing. The propensity for mammalian cells to produce single crystals using this system will allow for future structural analysis using microbeam and free-electron laser-based serial femtosecond crystallography [16, 17]. Furthermore, the ease with which the crystals can be generated following DNA transformation into mammalian cells suggests uses in other experimental areas, such as for generating high density in vivo sensors.

Whilst there has been described in the foregoing description preferred embodiments of the present invention, it will be understood by those skilled in the technology concerned that many variations or modifications in details of design or construction may be made without departing from the present invention.

REFERENCES

1. Baskaran, Y., Ng, Y. W., Selamat, W., Ling, F. T. & Manser, E. Group I and II mammalian PAKs have different modes of activation by Cdc42. *EMBO Rep* 13, 653-659 (2012).
2. Ha, B. H. et al. Type II p21-activated kinases (PAKs) are regulated by an autoinhibitory pseudosubstrate. *Proceedings of the National Academy of Sciences of the United States of America* 109, 16107-16112 (2012).
3. Redecke, L. et al. Natively inhibited *Trypanosoma brucei* cathepsin B structure determined by using an X-ray laser. *Science* 339, 227-230 (2013).
4. Koopmann, R. et al. In vivo protein crystallization opens new routes in structural biology. *Not. Methods* 9, 259-262 (2012).
5. Axford, D., Ji, X., Stuart, D. I. & Sutton, G. In cellulo structure determination of a novel cypovirus polyhedrin. *Acta Crystallogr D Biol Crystallogr* 70, 1435-1441 (2014).
6. Tsutsui, H. et al. A diffraction-quality protein crystal processed as an autophagic cargo. *Molecular cell* 58, 186-193 (2015).
7. Inokuma, Y., Kawano, M. & Fujita, M. Crystalline molecular flasks. *Nature chemistry* 3, 349-358 (2011).
8. Reid, B. S., Sargent, T. D. & Williams, T. Generation and characterization of a novel neural crest marker allele, Inka1-LacZ, reveals a role for Inka1 in mouse neural tube closure. *Developmental dynamics: an official publication of the American Association of Anatomists* 239, 1188-1196 (2010).
9. Luo, T. et al. Regulatory targets for transcription factor AP2 in *Xenopus* embryos. *Development, growth & differentiation* 47, 403-413 (2005).
10. Wang, W., Lim, L., Baskaran, Y., Manser, E. & Song, J. NMR binding and crystal structure reveal that intrinsically-unstructured regulatory domain auto-inhibits PAK4 by a mechanism different from that of PAK1. *Biochem. Biophys. Res. Commun.* 438, 169-174 (2013).
11. Wang, W., Lim, L., Baskaran, Y., Manser, E. & Song, J. NMR binding and crystal structure reveal that intrinsically-unstructured regulatory domain auto-inhibits PAK4 by a mechanism different from that of PAK1. *Biochemical and biophysical research communications* 438, 169-174 (2013).
12. Ryu, B J. et al. Discovery and the structural basis of a novel p21-activated kinase 4 inhibitor. *Cancer letters* 349, 45-50 (2014).
13. Staben, S. T. et al. Back pocket flexibility provides group II p21-activated kinase (PAK) selectivity for type I 1/2 kinase inhibitors. *J Med Chem* 57, 1033-1045 (2014).
14. Murray, B. W. et al. Small-molecule p21-activated kinase inhibitor PF-3758309 is a potent inhibitor of oncogenic signaling and tumor growth. *Proceedings of the National Academy of Sciences of the United States of America* 107, 9446-9451 (2010).
15. Guo, C. et al. Discovery of pyrroloaminopyrazoles as novel PAK inhibitors. *J Med Chem* 55, 4728-4739 (2012).
16. Schlichting, I. & Miao, J. Emerging opportunities in structural biology with X-ray free-electron lasers. *Curr Opin Struct Biol* 22, 613-626 (2012).
17. Sawaya, M. R. et al. Protein crystal structure obtained at 2.9 A resolution from injecting bacterial cells into an X-ray free-electron laser beam. *Proceedings of the National Academy of Sciences of the United States of America* 111, 12769-12774 (2014).

The invention claimed is:

1. A protein crystal comprising:
   (a) a first protein in crystal form having available space within a lattice in said protein crystal, wherein the first protein is a p21-activated kinase 4 (PAK4), or a catalytic domain thereof; and
   (b) a second protein in crystal form accommodated in the available space in the lattice of (a), wherein the second protein is an iBox of Inka1, the first and second proteins being co-expressed from one or more nucleic acid construct,
   wherein the available space in the lattice in said protein crystal further accommodates a moiety.

2. The protein crystal of claim 1, wherein the moiety is fused to iBox or iBox-C of Inka1, and has a molecular mass less than 30 kDa.

3. The protein crystal of claim 1, wherein the moiety further comprises a reporter molecule, and the reporter molecule comprises a molecule selected from the group consisting of a fluorescent protein, a tag recognized by a monoclonal antibody, and a genetically encoded biosensor.

4. The protein crystal of claim 1, wherein the protein crystal forms a hexagonal array with channels of 80 Å in diameter.

5. The protein crystal of claim 1, wherein the first protein is present at a ratio of about 1:1 relative to the second protein.

6. The protein crystal of claim 1, wherein the protein crystal is formed in cellulo in a mammalian cell.

7. The protein crystal of claim 1, wherein the protein crystal is more than 50 μm in length and comprises a crystal structure that is determined at a resolution of 3 Å or a resolution to a value that is below 3 Å.

8. The protein crystal of claim 1, wherein the moiety is a protein of interest.

9. A fusion protein, comprising:
(a) a first protein which, upon crystallization of the fusion protein, yields a protein crystal having available space in a lattice in said protein crystal, wherein the first protein is a p21-activated kinase 4 (PAK4), or a catalytic domain thereof; and
(b) a second protein which is an iBox of Inka1 and which, upon crystallization of the fusion protein, is accommodated in the available space in the lattice in said protein crystal, wherein the first and second proteins are co-expressed from one or more nucleic acid construct.

10. The fusion protein of claim 9, wherein the available space in the lattice in said protein crystal further accommodates a moiety, wherein the moiety is a protein of interest.

11. A method for producing either
(1) a protein crystal which comprises (a) a first protein in crystal form having available space within a lattice in said protein crystal, wherein the first protein is a p21-activated kinase 4 (PAK4), or a catalytic domain thereof; and (b) a second protein in crystal form accommodated in the available space in the lattice of (a), wherein the second protein is an iBox of Inka1, the first and second proteins being co-expressed from one or more nucleic acid construct, or
(2) a fusion protein which comprises (a) a first protein which, upon crystallization of the fusion protein, yields a protein crystal having available space in a lattice in said protein crystal, wherein the first protein is a p21-activated kinase 4 (PAK4), or a catalytic domain thereof; and (b) a second protein which is an iBox of Inka1 and which, upon crystallization of the fusion protein, is accommodated in the available space in the lattice in said protein crystal, wherein the first and second proteins are co-expressed from one or more nucleic acid construct, the method comprising:
culturing a host cell under conditions that permit production of the protein crystal or the fusion protein, wherein the first and second proteins are co-expressed from one or more nucleic acid construct, and wherein the available space in the lattice in said protein crystal or fusion protein further accommodates a moiety .

12. The method of claim 11, wherein either or both of co-expression and conditions for crystallization are carried out in vitro.

13. The method of claim 11, wherein the first protein is a PAK4 catalytic domain.

14. The method of claim 11, wherein the second protein is fused to a third protein, said third protein comprising a protein of interest having a molecular mass less than 30 kDa.

15. The method of claim 11, wherein the moiety is fused to a reporter molecule.

16. The method of claim 11, further comprising isolating and purifying the protein crystal or fusion protein, and obtaining structural data on the protein crystal or fusion protein.

17. The method of claim 11, wherein the host cell is a mammalian cell.

* * * * *

```
SEQUENCE LISTING

<160> NUMBER OF SEQ ID NOS: 25

<210> SEQ ID NO 1
<211> LENGTH: 38
<212> TYPE: PRT
<213> ORGANISM: Homo sapiens
<220> FEATURE:
<221> NAME/KEY: NON_TER
<222> LOCATION: (1)..(1)
<220> FEATURE:
<221> NAME/KEY: NON_TER
<222> LOCATION: (38)..(38)

<400> SEQUENCE: 1

Leu Pro Arg Gln Trp Gln Ser Leu Ile Glu Glu Ser Ala Arg Arg Pro
1               5                   10                  15

Lys Pro Leu Val Asp Pro Ala Cys Ile Thr Ser Ile Gln Pro Gly Ala
            20                  25                  30

Pro Lys Thr Ile Val Arg
        35

<210> SEQ ID NO 2
<211> LENGTH: 38
<212> TYPE: PRT
<213> ORGANISM: Xenopus laevis
<220> FEATURE:
<221> NAME/KEY: NON_TER
<222> LOCATION: (1)..(1)
<220> FEATURE:
<221> NAME/KEY: NON_TER
<222> LOCATION: (38)..(38)

<400> SEQUENCE: 2

Leu Pro Arg Gln Trp Gln Ser Leu Ile Glu Glu Ser Ala Lys Arg Pro
1               5                   10                  15

Lys Pro Leu Val Asp Pro Ser Tyr Ile Thr Thr Ile Lys His Val Pro
            20                  25                  30

Gln Lys Thr Ile Val Arg
        35

<210> SEQ ID NO 3
<211> LENGTH: 38
<212> TYPE: PRT
<213> ORGANISM: Homo sapiens
```

```
<220> FEATURE:
<221> NAME/KEY: NON_TER
<222> LOCATION: (1)..(1)
<220> FEATURE:
<221> NAME/KEY: NON_TER
<222> LOCATION: (38)..(38)

<400> SEQUENCE: 3

Glu Ala Glu Asp Trp Thr Ala Ala Leu Leu Asn Arg Gly Arg Ser Arg
1               5                   10                  15

Gln Pro Leu Val Leu Gly Asp Asn Cys Phe Ala Asp Leu Val His Asn
            20                  25                  30

Trp Met Glu Leu Pro Glu
        35

<210> SEQ ID NO 4
<211> LENGTH: 38
<212> TYPE: PRT
<213> ORGANISM: Xenopus laevis
<220> FEATURE:
<221> NAME/KEY: NON_TER
<222> LOCATION: (1)..(1)
<220> FEATURE:
<221> NAME/KEY: NON_TER
<222> LOCATION: (38)..(38)

<400> SEQUENCE: 4

Asp Ser Gln Asp Trp Thr Gly Cys Leu Leu Ser Gln Ser Arg Ser Arg
1               5                   10                  15

Gln Pro Leu Ile Leu Gly Asp Asn Ser Phe Ala Asp Leu Val Lys Gln
            20                  25                  30

Trp Met Asp Leu Pro Glu
        35

<210> SEQ ID NO 5
<211> LENGTH: 27
<212> TYPE: PRT
<213> ORGANISM: Homo sapiens
<220> FEATURE:
<221> NAME/KEY: NON_TER
<222> LOCATION: (1)..(1)

<400> SEQUENCE: 5

Pro Ala Asp Val Ser Arg Phe Ala Ala Leu Met Ser Cys Arg Ser Arg
1               5                   10                  15

Gln Pro Ile Ile Cys Asn Asp Val Ser Tyr Leu
            20                  25

<210> SEQ ID NO 6
<211> LENGTH: 28
<212> TYPE: PRT
<213> ORGANISM: Xenopus laevis
<220> FEATURE:
<221> NAME/KEY: NON_TER
<222> LOCATION: (1)..(1)

<400> SEQUENCE: 6

Ser Asp Ile Ala Glu Ala Ser Thr Asn Leu Leu Asn Cys Arg Ser Arg
1               5                   10                  15

Arg Pro Ile Ile Cys Asn Glu Gly Ala Gly Phe Leu
            20                  25
```

-continued

<210> SEQ ID NO 7
<211> LENGTH: 38
<212> TYPE: PRT
<213> ORGANISM: Artificial Sequence
<220> FEATURE:
<223> OTHER INFORMATION: iBox recombinant protein

<400> SEQUENCE: 7

Glu Ala Glu Asp Trp Thr Ala Ala Leu Leu Asn Arg Gly Arg Ser Arg
1               5                   10                  15

Gln Pro Leu Val Leu Gly Asp Asn Cys Phe Ala Asp Leu Val His Asn
            20                  25                  30

Trp Met Glu Leu Pro Glu
        35

<210> SEQ ID NO 8
<211> LENGTH: 24
<212> TYPE: PRT
<213> ORGANISM: Artificial Sequence
<220> FEATURE:
<223> OTHER INFORMATION: iBox24

<400> SEQUENCE: 8

Ala Glu Asp Trp Thr Ala Ala Leu Leu Asn Arg Gly Arg Ser Arg Gln
1               5                   10                  15

Pro Leu Val Leu Gly Asp Asn Cys
            20

<210> SEQ ID NO 9
<211> LENGTH: 24
<212> TYPE: PRT
<213> ORGANISM: Artificial Sequence
<220> FEATURE:
<223> OTHER INFORMATION: iBox24C

<400> SEQUENCE: 9

Arg Ser Arg Gln Pro Leu Val Leu Gly Asp Asn Cys Phe Ala Asp Leu
1               5                   10                  15

Val His Asn Trp Met Glu Leu Pro
            20

<210> SEQ ID NO 10
<211> LENGTH: 24
<212> TYPE: PRT
<213> ORGANISM: Artificial Sequence
<220> FEATURE:
<223> OTHER INFORMATION: iBox-C24

<400> SEQUENCE: 10

Val Ser Arg Phe Ala Ala Leu Met Ser Cys Arg Ser Arg Gln Pro Ile
1               5                   10                  15

Ile Cys Asn Asp Val Ser Tyr Leu
            20

<210> SEQ ID NO 11
<211> LENGTH: 14
<212> TYPE: PRT
<213> ORGANISM: Artificial Sequence
<220> FEATURE:
<223> OTHER INFORMATION: iBox14

<400> SEQUENCE: 11

Arg Gly Arg Ser Arg Gln Pro Leu Val Leu Gly Asp Asn Cys
1               5                   10

-continued

```
<210> SEQ ID NO 12
<211> LENGTH: 14
<212> TYPE: PRT
<213> ORGANISM: Artificial Sequence
<220> FEATURE:
<223> OTHER INFORMATION: PAK4 AID14

<400> SEQUENCE: 12

Gly Ser Ala Arg Arg Pro Lys Pro Leu Val Asp Pro Ala Cys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: PAK4cat substrate peptide

<400> SEQUENCE: 13

Arg Arg Arg Arg Arg Ser Trp Tyr Phe Asp Gly
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Raf13p

<400> SEQUENCE: 14

Pro Arg Gly Gln Arg Asp Ser Ser Tyr Tyr Trp Glu Ile
1               5                   10

<210> SEQ ID NO 15
<211> LENGTH: 23
<212> TYPE: PRT
<213> ORGANISM: Artificial Sequence
<220> FEATURE:
<223> OTHER INFORMATION: iBox 23mer

<400> SEQUENCE: 15

Ala Glu Asp Trp Thr Ala Ala Leu Leu Asn Arg Gly Arg Ser Arg Gln
1               5                   10                  15

Pro Leu Val Leu Gly Asp Trp
            20

<210> SEQ ID NO 16
<211> LENGTH: 10
<212> TYPE: PRT
<213> ORGANISM: Homo sapiens
<220> FEATURE:
<221> NAME/KEY: NON_TER
<222> LOCATION: (1)..(1)
<220> FEATURE:
<221> NAME/KEY: DOMAIN
<222> LOCATION: (1)..(10)
<223> OTHER INFORMATION: core Inka1 sequence
<220> FEATURE:
<221> NAME/KEY: NON_TER
<222> LOCATION: (10)..(10)

<400> SEQUENCE: 16

Arg Ser Arg Gln Pro Leu Val Leu Gly Asp
1               5                   10
```

```
<210> SEQ ID NO 17
<211> LENGTH: 7
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Replacement of serine

<400> SEQUENCE: 17

Arg Arg Gly Ala Ile Lys Gln
1               5

<210> SEQ ID NO 18
<211> LENGTH: 7
<212> TYPE: PRT
<213> ORGANISM: Homo sapiens
<220> FEATURE:
<221> NAME/KEY: NON_TER
<222> LOCATION: (1)..(1)
<220> FEATURE:
<221> NAME/KEY: MISC_FEATURE
<222> LOCATION: (4)..(4)
<223> OTHER INFORMATION: Replacement of serine
<220> FEATURE:
<221> NAME/KEY: NON_TER
<222> LOCATION: (7)..(7)

<400> SEQUENCE: 18

Arg Arg Asn Ala Ile His Asp
1               5

<210> SEQ ID NO 19
<211> LENGTH: 8
<212> TYPE: PRT
<213> ORGANISM: Homo sapiens
<220> FEATURE:
<221> NAME/KEY: NON_TER
<222> LOCATION: (1)..(1)
<220> FEATURE:
<221> NAME/KEY: NON_TER
<222> LOCATION: (8)..(8)

<400> SEQUENCE: 19

Arg Ser Arg Gln Pro Leu Val Leu
1               5

<210> SEQ ID NO 20
<211> LENGTH: 8
<212> TYPE: PRT
<213> ORGANISM: Homo sapiens
<220> FEATURE:
<221> NAME/KEY: NON_TER
<222> LOCATION: (1)..(1)
<220> FEATURE:
<221> NAME/KEY: NON_TER
<222> LOCATION: (8)..(8)

<400> SEQUENCE: 20

Arg Pro Lys Pro Leu Val Asp Pro
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic sequence
```

```
<400> SEQUENCE: 21

Arg Arg Arg Arg Ser Trp Tyr Phe Asp Gly
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic sequence

<400> SEQUENCE: 22

Ser Ala Arg Arg Pro Lys Ser Leu Val Asp Pro Ala Asp
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic sequence

<400> SEQUENCE: 23

Pro Arg Gly Gln Arg Asp Ser Ser Tyr Tyr Trp Glu Lys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic sequence

<400> SEQUENCE: 24

Arg Gly Arg Ser Arg Gln Ser Leu Val Leu Gly Asp Asp
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic sequence

<400> SEQUENCE: 25

Ser Leu Arg Ser Arg Gln Ser Ile Ile Tyr Asn Asp Val
1               5                   10
```